(12) United States Patent
Gottlieb et al.

(10) Patent No.: US 11,960,383 B2
(45) Date of Patent: Apr. 16, 2024

(54) SYSTEMS AND METHODS FOR SOFTWARE DESIGN CONTROL AND QUALITY ASSURANCE

(71) Applicant: Akili Interactive Labs, Inc., Boston, MA (US)

(72) Inventors: Carl Gottlieb, Fairfax, CA (US); Jason Trees, Dedham, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

(21) Appl. No.: 17/117,050

(22) Filed: Dec. 9, 2020

(65) Prior Publication Data
US 2021/0311864 A1 Oct. 7, 2021

Related U.S. Application Data

(60) Provisional application No. 63/003,673, filed on Apr. 1, 2020.

(51) Int. Cl.
*G06F 11/36* (2006.01)
*G16H 20/00* (2018.01)

(52) U.S. Cl.
CPC ...... *G06F 11/3664* (2013.01); *G06F 11/3688* (2013.01); *G06F 11/3692* (2013.01); *G16H 20/00* (2018.01)

(58) Field of Classification Search
CPC ..... G06F 11/30–3696; A61B 5/16–168; A61B 5/7264–7267; A61B 5/7271–7275; A61B 5/7282; G16H 20/00; G16H 20/70
See application file for complete search history.

(56) References Cited

U.S. PATENT DOCUMENTS 6,652,457 B1    11/2003  Skiba et al.
7,299,451 B2    11/2007  Dygon et al.
(Continued)

FOREIGN PATENT DOCUMENTS

TW      M496157 U      2/2015
TW      I594114 B      8/2017
WO      WO-2018081134 A1 *  5/2018  ............. A61B 5/167

OTHER PUBLICATIONS

Search report, Taiwan application No. 110112131, dated Nov. 2, 2022. Taiwan Intellectual Property Office, Taipei City, TW.
(Continued)

*Primary Examiner* — Todd Aguilera
(74) *Attorney, Agent, or Firm* — Gregory Finch; Finch Paolino, LLC

(57) ABSTRACT

A design control architecture and software quality assurance system for analyzing stimulus-response patterns in user activity data. A design control architecture and software quality assurance system may process user activity data according to a classifier model to assess an impact of an incremental design change to one or more quality measures of a software product. In accordance with certain embodiments the one or more quality measures may include one or more efficacy, safety, and/or performance metrics associated with one or more features of the software product. In certain embodiments, the software product may comprise a digital health intervention or software as a medical device product.

14 Claims, 13 Drawing Sheets

(56) References Cited

U.S. PATENT DOCUMENTS

| | | | |
|---|---|---|---|
| 8,086,280 B2* | 12/2011 | Smith | H04B 7/155 |
| | | | 455/571 |
| 8,286,143 B2* | 10/2012 | Garimella | G06F 11/3688 |
| | | | 717/131 |
| 9,021,441 B2 | 4/2015 | Yawalker et al. | |
| 9,336,127 B2* | 5/2016 | Koneru | G06F 11/3684 |
| 9,483,393 B1 | 11/2016 | Suttle et al. | |
| 9,558,098 B1 | 1/2017 | Alshayeb et al. | |
| 9,600,405 B1 | 3/2017 | Dunn et al. | |
| 9,857,858 B2 | 1/2018 | Bodas et al. | |
| 10,946,165 B2* | 3/2021 | Metzger | A61B 5/6814 |
| 11,126,635 B2 | 9/2021 | Behzadi et al. | |
| 11,201,937 B2* | 12/2021 | Carley | H04L 67/55 |
| 2002/0147620 A1 | 10/2002 | Walsh | |
| 2003/0009740 A1 | 1/2003 | Lan | |
| 2009/0125891 A1* | 5/2009 | Garimella | G06F 11/3612 |
| | | | 717/131 |
| 2010/0023928 A1 | 1/2010 | Hentschel et al. | |
| 2010/0159823 A1* | 6/2010 | Smith | H04B 7/155 |
| | | | 455/7 |
| 2010/0251027 A1 | 9/2010 | Yawalkar et al. | |
| 2012/0167055 A1 | 6/2012 | Yokoi | |
| 2014/0237451 A1* | 8/2014 | Koneru | G06F 11/3692 |
| | | | 717/124 |
| 2015/0164377 A1 | 6/2015 | Nathan et al. | |
| 2017/0293356 A1* | 10/2017 | Khaderi | A61B 3/024 |
| 2018/0113802 A1* | 4/2018 | Yeddnapuddi | G06F 11/3692 |
| 2018/0221620 A1* | 8/2018 | Metzger | A61N 1/0484 |
| 2020/0060603 A1* | 2/2020 | Bower | G16H 20/70 |
| 2021/0176326 A1* | 6/2021 | Carley | G06F 9/546 |

OTHER PUBLICATIONS

Lee, Ming-Chang. "Software Quality Factors and Software Quality Metrics to Enhance Software Quality Assurance." British Journal of Applied Science and Technology 4(21): 3069-3095. Jun. 2, 2014. ScienceDomain international, www.sciencedomain.org.
International Search Report, International application No. PCT/US2021/025377, dated Jun. 30, 2021. ISA/US, Alexandria, VA.
Written Opinion of the International Searching Authority, International application No. PCT/US2021/025377, dated Jun. 30, 2021. ISA/US, Alexandria, VA.
Translation, Office Action dated Oct. 31, 2022. Taiwan application No. 110112131. Intellectual Property Office, Taipei City, TW.

* cited by examiner

SYSTEMS AND METHODS FOR SOFTWARE DESIGN CONTROL AND QUALITY ASSURANCE

CROSS-REFERENCE TO RELATED APPLICATIONS

This application claims priority benefit of U.S. Provisional Application Ser. No. 63/003,673 filed Apr. 1, 2020, the entirety of which is hereby incorporated herein at least by reference.

FIELD

The present disclosure relates to the field of software quality assurance systems; in particular, systems and methods for procedural analysis of stimulus-input patterns in user testing data to assess, measure and/or validate one or more performance metrics associated with a program code build.

BACKGROUND

Quality assurance is often an integral part of software development. For example, quality assurance personnel may test newly developed software, identify defects contained within the software, and determine whether the software is of high enough quality to be released to end users. Software quality assurance may encompass the entire software development process, including requirements definition, software design, coding, code reviews, source code control, software configuration management, testing, release management and product integration. The software quality assurance process may be organized into goals, commitments, abilities, activities, measurements and verification.

Software is an increasingly critical area of healthcare product development. An expanding area of healthcare product development is in the area of digital health interventions (i.e. interventions delivered via digital technologies such as smartphones, mobile computing devices, wearable electronic devices, and the like) to provide effective, cost-effective, safe, and scalable interventions to improve health and healthcare. Digital health interventions (DHI) and Software as a Medical Device (SaMD) can be used to promote healthy behaviors, improve outcomes in people with long term conditions such as cardiovascular disease, diabetes and mental health conditions and provide remote access to effective treatments; for example, computerized cognitive behavioral therapy for mental health and somatic problems. Software as a Medical Device (SaMD) is defined by the International Medical Device Regulators Forum (IMDRF) as "software intended to be used for one or more medical purposes that perform these purposes without being part of a hardware medical device." DHIs are often complex interventions with multiple components, and many have multiple aims including enabling users to be better informed about their health, share experiences with others in similar positions, change perceptions and cognitions around health, assess and monitor specified health states or health behaviors, titrate medication, clarify health priorities and reach treatment decisions congruent with these, and improve communication between patients and health care professionals (HCP). Active components may include information, psychoeducation, personal stories, formal decision aids, behavior change support, interactions with HCP and other patients, self-assessment or monitoring tools (questionnaires, wearables, monitors, and effective theory-based psychological interventions developed for face-to-face delivery such as cognitive behavioral therapy or mindfulness training). Certain DHI and SaMD products may include software that is itself directly therapeutically active in treating and/or targeting one or more neurological circuits related to one or more neurological, psychological and/or somatic conditions, diseases, and/or disorders, rather than just being a component of overall treatment.

The unique nature of SaMD and DHI software products, as compared to business or consumer software products, poses specific challenges with respect to software development and software quality assurance policies, processes and standards. Through applied effort, ingenuity, and innovation, Applicant has identified deficiencies of prior art solutions and has developed a solution that is embodied by the present disclosure, which is described in detail below.

SUMMARY

In order to provide a basic understanding of the invention, the following is a simplified summary of certain embodiments thereof. This summary is not an extensive and is not intended to identify key/critical elements of the invention or to delineate the scope of the invention. Its sole purpose is to present embodiments of the invention in a simplified form as a prelude to the more detailed description that is further below.

An object of the present disclosure includes a design control architecture and quality assurance system for analyzing stimulus-response patterns in user activity data to assess efficacy, safety, and/or performance of one or more feature of a software product. Further objects include a design control architecture and quality assurance system for assessing the impact of an incremental design change on the efficacy, safety, and/or performance of a software product. Certain aspects of the present disclosure provide for a design control architecture and quality assurance system/method for monitoring and configuring one or more software development processes for a DHI or SaMD, including software design, coding, code reviews, source code control, software configuration management, testing, release management and product integration.

An object of the present disclosure includes systems and methods for measuring the performance of a DHI or SaMD. Further objects include systems and methods for measuring and/or quantifying an amount of therapeutic activity and/or effectiveness of a DHI or SaMD. Certain aspects of the present disclosure may include systems and methods for measuring and/or validating the effectiveness of a DHI or SaMD to treat and/or target one or more neurological circuits related to one or more neurological, psychological and/or somatic conditions, diseases, and/or disorders of a user. Further objects include systems and methods for measuring and/or quantifying an amount of therapeutic activity and/or effectiveness of one or more individual features or aspects of a DHI or SaMD. Further objects include systems and methods for assessing the impact of an incremental design change on the effectiveness of a DHI or SaMD to treat and/or target one or more neurological circuits related to one or more neurological, psychological and/or somatic conditions, diseases, and/or disorders of a user.

An object of the present disclosure includes systems and methods for analyzing one or more patterns in user activity data derived from one or more instances or sessions of a DHI or SaMD product. In accordance with certain embodiments, the one or more patterns may include one or more clinically validated stimulus-response pattern. Certain embodiments of the present disclosure may include a machine learning framework, a classifier model, and/or classification algorithm for classifying and/or mapping user inputs into one or more categories. In certain embodiments, the one or more categories may correspond to one or more safety, efficacy, or performance aspects of a DHI or SaMD product.

Certain aspects of the present disclosure provide for a processor-implemented method for software quality assurance, comprising presenting, with a computing device, a testing instance of a software build to a user, the software build comprising at least one test feature configured to present one or more computerized stimuli or interaction to the user via a graphical user interface; receiving, with the computing device, one or more user inputs in response to the one or more computerized stimuli or interaction, the one or more user inputs comprising user activity data; receiving, with a processor communicably engaged with the computing device, the user activity data; processing, with the processor, the user activity data according to at least one classification model to classify the activity data, the at least one classification model being configured to classify one or more variables associated with a targeted stimulus-response pattern; analyzing a stimulus-input pattern between the user activity data and the one or more computerized stimuli or interactions to determine one or more performance metrics for the software build, the one or more performance metrics comprising a measure of efficacy of the at least one test feature; and evaluating the software build according to the one or more performance metrics to determine a pass/fail status of the software build according to a minimum performance threshold.

In accordance with said aspects of the present disclosure, said method for software quality assurance may further comprise evaluating the software build according to the one or more performance metrics to determine a pass/fail status of the at least one test feature according to the minimum performance threshold. The method may further comprise comparing the one or more performance metrics for the software build to one or more performance metrics from a prior or subsequent software build to determine a measure of change in the one or more performance metrics. In certain embodiments, the one or more performance metrics comprise a measure of active therapeutic delivery received by the user in response to the testing instance of the software build.

In accordance with said aspects of the present disclosure, the method for software quality assurance may further comprise presenting the user activity data and the one or more performance metrics to an administrator user via a graphical user interface, the graphical user interface being configured to receive one or more user queries for evaluation of the at least one test feature. In certain embodiments, the one or more performance metrics comprise a measure of safety of the at least one test feature and/or the software build. In certain embodiments, the one or more computerized stimuli or interaction may be configured to actively treat or target one or more neurological, psychological or somatic condition of the user. In accordance with said embodiments, the measure of efficacy may correspond to a measure of therapeutic treatment for the one or more neurological, psychological or somatic condition of the user. In further accordance with said embodiments, the at least one classification model may be configured to classify one or more variables associated with treating or targeting the one or more neurological, psychological and/or somatic condition of the user.

Further aspects of the present disclosure provide for a processor-implemented system for software quality assurance, comprising at least one server comprising at least one processor, the at least one server being communicably engaged with one or more computing devices to receive a plurality of user-generated inputs in response to one or more computerized stimuli or interactions being presented within a testing instance of a software build, the plurality of user-generated inputs comprising user activity data; and a non-transitory computer readable storage medium operably engaged with the at least one processor and encoded with computer-executable instructions that, when executed by the at least one processor, perform one or more operations for: receiving the user activity data; processing the user activity data according to at least one classification model to classify the user activity data, the at least one classification model being configured to classify one or more variables associated with a targeted stimulus-response pattern; analyzing at least one stimulus-input pattern between the user activity data and the one or more computerized stimuli or interactions to determine one or more performance metrics for the software build, the one or more performance metrics comprising a measure of safety, performance or efficacy of at least one test feature; and evaluating the software build according to the one or more performance metrics to determine a pass/fail status of the software build according to a minimum performance threshold.

In accordance with said aspects of the present disclosure, the system for software quality assurance may be further configured wherein the classification model comprises at least one machine learning framework comprising an ensemble learning model and/or a supervised learning model. In accordance with certain embodiments, the system may be further configured wherein the classification model comprises a random forest algorithm or a random decision forest algorithm. The system may be further configured wherein the at least one server is communicably engaged with at least one external server via an application programming interface to receive the plurality of user-generated inputs.

In accordance with certain embodiments, the system for software quality assurance may be further configured wherein the computer-executable instructions further comprise operations for presenting the user activity data and the one or more performance metrics to an administrator user via a graphical user interface. The system may be further configured wherein the computer-executable instructions further comprise operations for comparing the one or more performance metrics for the software build to one or more performance metrics from a prior or subsequent software build to determine a measure of change in the one or more performance metrics. The system may be further configured wherein the computer-executable instructions further comprise operations for determining a measure of active therapeutic delivery received by the user in response to the one or more computerized stimuli or interactions.

In accordance with certain embodiments, the system for software quality assurance may be further configured wherein the computer-executable instructions further comprise operations for comparing the one or more performance metrics for the software build to one or more performance metrics from a prior or subsequent software build to analyze a causal relationship between the at least one test feature and the one or more performance metrics. The system may be further configured wherein the at least one test feature comprises a design change or variation from a previous version of the at least one test feature. In accordance with certain embodiments, the computer-executable instructions may further comprise operations for analyzing a causal relationship between the design change or variation and the one or more performance metrics.

Still further aspects of the present disclosure provide for a non-transitory computer-readable medium encoded with instructions for commanding one or more processors to execute operations for software quality assurance, the operations comprising receiving a plurality of user-generated inputs in response to one or more computerized stimuli or interactions being presented within a testing instance of a software build, the plurality of user-generated inputs comprising user activity data; processing the user activity data according to at least one classification model to classify the user activity data, the at least one classification model being configured to classify one or more variables associated with a targeted stimulus-response pattern; analyzing at least one stimulus-input pattern between the user activity data and the one or more computerized stimuli or interactions to determine one or more performance metrics for the software build, the one or more performance metrics comprising a measure of safety, performance or efficacy of at least one test feature; and evaluating the software build according to the one or more performance metrics to determine a pass/fail status of the software build according to a minimum performance threshold.

Still further aspects of the present disclosure provide for a method for software quality assurance, comprising presenting, with a user computing device via a graphical user interface, an instance of a software build to a user, the software build comprising at least one feature comprising one or more computerized stimuli or interactions configured to elicit an expected stimulus-input pattern from the user in response to the one or more computerized stimuli or interactions; receiving, with at least one sensor communicably engaged with the user computing device, a plurality of user inputs in response to presenting the one or more computerized stimuli or interactions within the instance of the software build, the plurality of user inputs comprising user activity data for a session of the software build; receiving, with a processor communicably engaged with the computing device, the user activity data; processing, with the processor, the user activity data according to at least one data model to determine one or more actual stimulus-input pattern for each user input in the plurality of user inputs; comparing the one or more actual stimulus-input pattern for each user input in the plurality of user inputs to the expected stimulus-input pattern for the at least one feature to determine a total number of instances in which the one or more actual stimulus-input pattern was reflective of the expected stimulus-input pattern within the session of the software build; calculating, with the processor, at least one output value for the user activity data according to the at least one data model, the at least one output value comprising a qualitative or quantitative degree of model fit for the at least one feature; and determining a pass/fail status for the software build according to the at least one output value.

In accordance with said aspects of the present disclosure, said method for software quality assurance may further comprise calculating a measure of net therapeutic activity within the session of the software build according to the total number of instances in which the one or more actual stimulus-input pattern was reflective of the expected stimulus-input pattern. The method may further comprise calculating a measure of active therapeutic delivery for the at least one feature within the session of the software build according to the total number of instances in which the one or more actual stimulus-input pattern was reflective of the expected stimulus-input pattern. In accordance with certain embodiments, the at least one data model may comprise a classification model configured to classify one or more variables associated with one or more performance, safety or efficacy parameters. In accordance with certain embodiments, the method may further comprise determining a pass/fail status for the at least one feature according to the at least one output value. The method may further comprise comparing the at least one output value to at least one prior output value associated with at least one prior version of the software build to determine a measure of change attributable to the at least one feature. The method may further comprise comparing the measure of net therapeutic activity within the session of the software build to at least one prior measure of net therapeutic activity associated with at least one prior version of the software build to determine a measure of change attributable to the at least one feature. The method may further comprise determining the pass/fail status for the software build according to the measure of net therapeutic activity within the session of the software build. The method may further comprise determining the pass/fail status for the software build according to the measure of active therapeutic delivery for the at least one feature within the session of the software build.

Still further aspects of the present disclosure provide for a system for software quality assurance, comprising a processor; and a non-transitory computer readable storage medium communicably engaged with the processor and encoded with processor-executable instructions that, when executed, cause the processor to perform one or more operations comprising presenting a graphical user interface comprising an instance of a software build, wherein the software build comprises at least one feature comprising one or more computerized stimuli or interactions configured to elicit an expected stimulus-input pattern from a user in response to the one or more computerized stimuli or interactions; receiving a plurality of user activity data for a session of the software build, wherein the plurality of user activity data comprises a plurality of user inputs in response to the one or more computerized stimuli or interactions; processing the plurality of user activity data according to at least one data model to determine one or more actual stimulus-input pattern for each user input in the plurality of user inputs; comparing the one or more actual stimulus-input pattern for each user input in the plurality of user inputs to the expected stimulus-input pattern for the at least one feature to determine a total number of instances in which the one or more actual stimulus-input pattern was reflective of the expected stimulus-input pattern within the session of the software build; calculating at least one output value for the plurality of user activity data according to the at least one data model, wherein the at least one output value comprises a qualitative or quantitative degree of model fit for the at least one feature; and determining a pass/fail status for the software build according to the at least one output value.

In accordance with said aspects of the present disclosure, the system for software quality assurance may be further configured wherein the one or more operations further comprise calculating a measure of net therapeutic activity within the session of the software build according to the total number of instances in which the one or more actual stimulus-input pattern was reflective of the expected stimulus-input pattern. In certain embodiments, the one or more operations may further comprise calculating a measure of active therapeutic delivery for the at least one feature within the session of the software build according to the total number of instances in which the one or more actual stimulus-input pattern was reflective of the expected stimulus-input pattern. In certain embodiments, the at least one data model may comprise a classification model configured to classify one or more variables associated with one or more performance, safety or efficacy parameters. In certain embodiments, the one or more operations may further comprise determining a pass/fail status for the at least one feature according to the at least one output value. In certain embodiments, the one or more operations may further comprise comparing the at least one output value to at least one prior output value associated with at least one prior version of the software build to determine a measure of change attributable to the at least one feature.

In certain embodiments, the one or more operations may further comprise comparing the measure of net therapeutic activity within the session of the software build to at least one prior measure of net therapeutic activity associated with at least one prior version of the software build to determine a measure of change attributable to the at least one feature. In certain embodiments, the one or more operations may further comprise determining the pass/fail status for the software build according to the measure of net therapeutic activity within the session of the software build. In certain embodiments, the one or more operations may further comprise determining the pass/fail status for the software build according to the measure of active therapeutic delivery for the at least one feature within the session of the software build. In certain embodiments, the one or more operations may further comprise determining the pass/fail status for the software build according to at least one safety parameter associated with the one or more computerized stimuli or interactions.

Still further aspects of the present disclosure provide for a non-transitory computer-readable medium encoded with instructions for commanding one or more processors to execute operations for software quality assurance, the operations comprising presenting a graphical user interface comprising an instance of a software build, wherein the software build comprises at least one feature comprising one or more computerized stimuli or interactions configured to elicit an expected stimulus-input pattern from a user in response to the one or more computerized stimuli or interactions; receiving a plurality of user activity data for a session of the software build, wherein the plurality of user activity data comprises a plurality of user inputs in response to the one or more computerized stimuli or interactions; processing the plurality of user activity data according to at least one data model to determine one or more actual stimulus-input pattern for each user input in the plurality of user inputs; comparing the one or more actual stimulus-input pattern for each user input in the plurality of user inputs to the expected stimulus-input pattern for the at least one feature to determine a total number of instances in which the one or more actual stimulus-input pattern was reflective of the expected stimulus-input pattern within the session of the software build; calculating at least one output value for the plurality of user activity data according to the at least one data model, wherein the at least one output value comprises a qualitative or quantitative degree of model fit for the at least one feature; and determining a pass/fail status for the software build according to the at least one output value.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be recognized by those skilled in the art that such equivalent structures do not depart from the spirit and scope of the invention.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
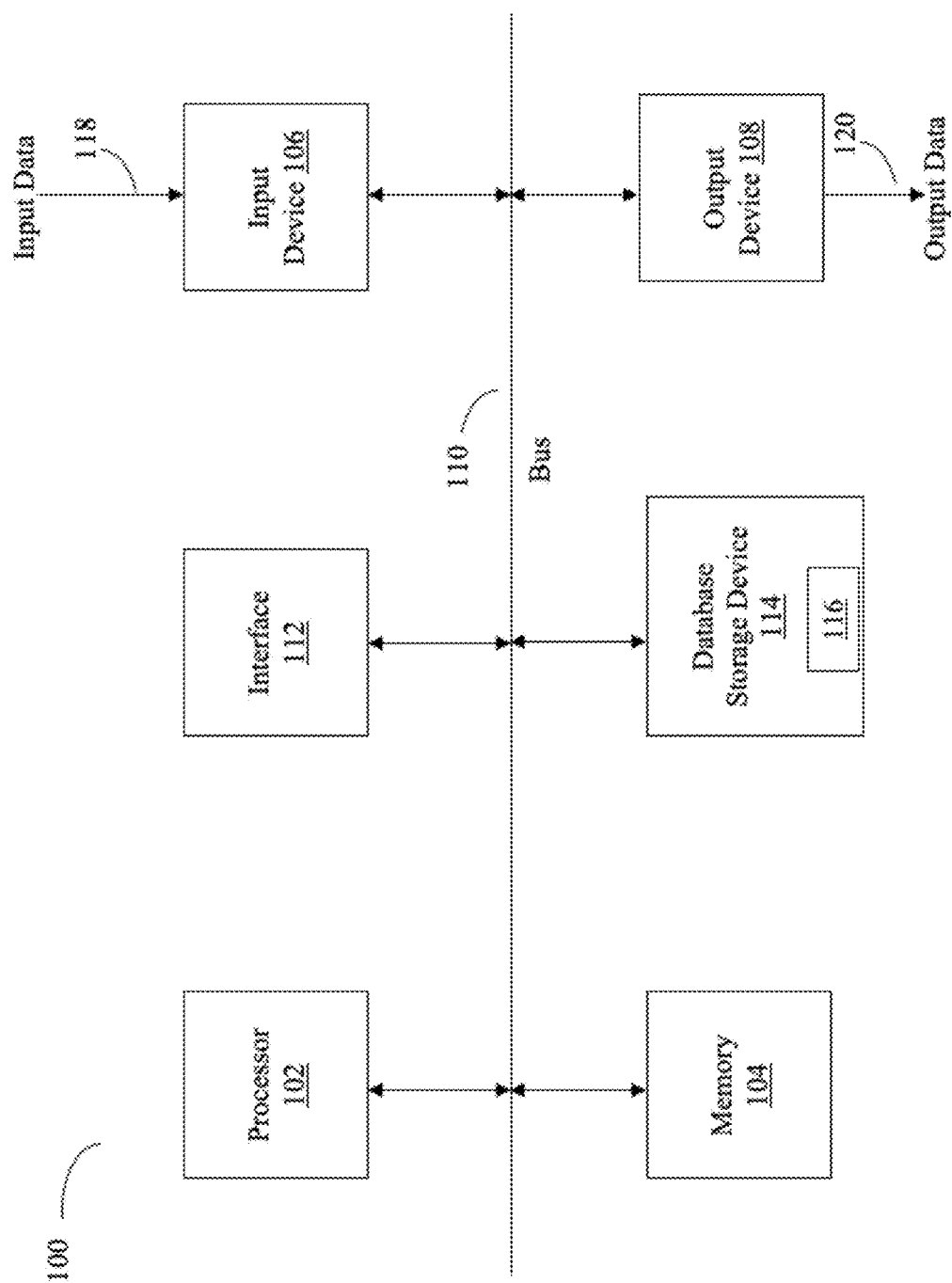
FIG. 1 is a functional block diagram of an exemplary computing system through which certain aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, devices, systems and non-transitory computer-readable media having instructions stored thereon to enable one or more said methods, devices and systems for presenting, with a computing device, a testing instance of a software build to a user, the software build comprising at least one test feature configured to present one or more computerized stimuli or interaction to the user via a graphical user interface; receiving, with the computing device, one or more user inputs in response to the one or more computerized stimuli or interaction, the one or more user inputs comprising user activity data; receiving, with a processor communicably engaged with the computing device, the user activity data; processing, with the processor, the user activity data according to at least one classification model to classify the activity data, the at least one classification model being configured to classify one or more variables associated with a targeted stimulus-response pattern; analyzing a stimulus-input pattern between the user activity data and the one or more computerized stimuli or interactions to determine one or more performance metrics for the software build, the one or more performance metrics comprising a measure of efficacy of the at least one test feature; and evaluating the software build according to the one or more performance metrics to determine a pass/fail status of the software build according to a minimum performance threshold.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "software build," refers to a version, artifact and/or compilation of program code comprising a software program or product and/or one or more component(s) or subcomponent(s) of a software program or product. In certain embodiments, a "software build" refers to a version, artifact and/or compilation of program code that is the subject of one or more software quality assurance processes in association with a software program. In certain embodiments, a "software build" refers to a version, artifact and/or compilation of program code that is pending release or publication in association with a software product.

As used herein, the term "toolchain," refers to any set of programming tools that are used to perform one or more software development task(s) and/or to create a software product, which may include another computer program and/or a set of related programs. In certain embodiments, programming tools comprising a toolchain may be executed consecutively such that the output or resulting environment state of each tool becomes the input or starting environment state for the next tool. In certain embodiments, the programming tools comprising the toolchain may comprise a set of related programming tools that may or may not be executed consecutively.

As used herein, the term "stimulus," refers to a sensory event configured to evoke a specified functional response from an individual. The degree and type of response can be quantified based on the individual's interactions with a measuring component (including using sensor devices or other measuring components).

As used in certain examples herein, the term "user activity data" refers to data collected from measures of an interaction of a user with a software program, product and/or platform.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus (presented, e.g., as an auditory computerized adjustable element or an element of a computerized auditory task) or initiate other auditory-based interaction with the user, and/or to present vibrational stimuli (presented, e.g., as a vibrational computerized adjustable element or an element of a computerized vibrational task) or initiate other vibrational-based interaction with the user, and/or to present tactile stimuli (presented, e.g., as a tactile computerized adjustable element or an element of a computerized tactile task) or initiate other tactile-based interaction with the user, and/or to present visual stimuli or initiate other visual-based interaction with the user.

In an example where the computing device is configured to present visual CSI, the CSI can be rendered as at least one user interface to be presented to a user. In some examples, the at least one user interface is configured for measuring responses as the user interacts with a CSI computerized element rendered at the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

As used in certain examples herein, the term "user" encompasses one or more of an end user and/or test user of a software program, product and/or platform and may further include: a patient being engaged with a software program, product or platform for a targeted medical or personal wellness purpose; a participant in a clinical trial, study or evaluation of a software program, product or platform; a user being engaged with a software program, product or platform for the purpose of evaluating or developing one or more technical, clinical, and/or functional aspects of a digital health intervention and/or a software as a medical device program, product or platform.

As used herein the terms "digital health intervention (DHI)" and "software as a medical device (SaMD)" may be used interchangeably and encompass any software program, product, or platform, including any software/hardware combination, being designed and/or utilized for any general or targeted medical or personal wellness purpose, including but not limited to the treatment, diagnosis, management, prevention, cure, or generation/provision of clinical/health/wellness insights or recommendations to one or more users for one or more medical, health or personal wellness purpose; including any software program, product, or platform, including any software/hardware combination, being designed and/or utilized to promote healthy behaviors, improve outcomes in people with long term conditions such as cardiovascular disease, diabetes and mental health conditions and provide remote access to effective treatments; for example, computerized cognitive behavioral therapy for mental health and somatic problems; and may further encompass one or more software program, product or platform, including any product(s), program(s) and/or platform (s) that incorporate any combination of hardware and software, that is/are directly therapeutically active in treating and/or targeting one or more neurological circuits related to one or more neurological, psychological and/or somatic conditions, diseases, and/or disorders, rather than just being a component of overall treatment.

All definitions, as defined and used herein, should be understood to control over dictionary definitions, definitions in documents incorporated by reference, and/or ordinary meanings of the defined terms. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

An exemplary system, method, and non-transitory computer readable media according to the principles herein provides for a design control architecture and quality assurance system for analyzing stimulus-response patterns in user activity data to assess the efficacy, safety, and/or performance of one or more features of a software product. In certain embodiments, the software product is configured as a DHI or SaMD. In accordance with certain embodiments, a design control architecture and quality assurance system are configured to process user activity data according to a classifier model in order to assess the impact of an incremental design change to efficacy, safety, and/or performance of a software product. An exemplary system and method may be configured to control or inform one or more software development processes associated with a software program, platform and/or product. The one or more software development processes may include one or more of software design, requirements analysis, feature testing, build testing, code reviews, source code control, quality control/assurance, software configuration management, testing, release management and/or product integration.

An exemplary system, method, and non-transitory computer readable media according to the principles herein provides for analyzing one or more patterns in user activity data from one or more instances or sessions of a DHI or SaMD product. In accordance with certain embodiments, the one or more patterns may include a procedural analysis to determine a measure of conformity with one or more clinically validated stimulus-response patterns. Certain embodiments of the present disclosure may include a machine learning framework, a classifier model, and/or classification algorithm for classifying and/or mapping user inputs into one or more categories. In certain embodiments, the one or more categories may correspond to one or more safety, efficacy, and/or performance aspects of a DHI or SaMD product.

An exemplary system, method, and non-transitory computer readable media according to the principles herein includes a system and method for measuring the performance of a DHI or SaMD. In accordance with certain embodiments, systems and methods of the present disclosure are configured to process user activity data according to a classifier model to measure and/or quantify an amount of therapeutic activity and/or effectiveness of a DHI or SaMD. In an example herein, a system, method, and non-transitory computer readable media provides for measuring and/or validating the effectiveness of a DHI or SaMD to treat and/or target one or more neurological circuits related to one or more neurological, psychological and/or somatic conditions, diseases, and/or disorders of a user. In accordance with such example(s), measuring and/or validating the effectiveness of a DHI or SaMD may further include measuring and/or quantifying an amount of therapeutic activity and/or effectiveness of one or more individual features or aspects of the DHI or SaMD. In an example herein, a system, method, and non-transitory computer readable media provides for analyzing the impact of an incremental design change on the effectiveness of a DHI or SaMD to treat and/or target one or more neurological circuits related to one or more neurological, psychological and/or somatic conditions, diseases, and/or disorders of a user.

A system, method, and computer platform product according to the principles herein enables a manufacturer of a software product to provide user activity data from one or more instances or sessions of the software product to a cloud server configured to analyze one or more patterns in user activity data. The system is configured to process the user activity data to determine a measure of conformity with one or more clinically validated stimulus-response patterns and provide a quantified analysis of one or more safety, efficacy, or performance aspects of the software product. In accordance with certain embodiments, the manufacturer of the software product may utilize the resulting analysis to inform or control one or more software development processes for the software product including, but not limited to, software design, requirements analysis, feature testing, build testing, code reviews, source code control, quality control/assurance, software configuration management, testing, release management and/or product integration.

Aspects of the present disclosure provide for a design control architecture and software quality assurance system for analyzing stimulus-response patterns in user activity data. Exemplary embodiments of the present disclosure provide for a design control architecture and software quality assurance system configured to process user activity data received from a user device executing an instance of a software build and process the user activity data according to a classifier model and processing framework to enable a developer user to assess the impact of an incremental design change to one or more quality measures of a software product. In accordance with certain embodiments, the one or more quality measures may include one or more efficacy, safety, and/or performance metrics associated with one or more features of the software product. In accordance with various embodiments, the design control architecture and software quality assurance system enables a developer of a software product comprising a digital health intervention or software as a medical device product to perform qualitative and/or quantitative analysis of one or more safety, efficacy and/or performance metrics of the software product and specific features thereof.

Turning now descriptively to the drawings, in which similar reference characters denote similar elements throughout the several views, FIG. 1 depicts a computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, a memory 104, an input device 106 for receiving input data 118 and an output device 108 that produces output data 120 coupled together with at least one bus 110. In certain embodiments, input device 106 and output device 108 could be the same device. An interface 112 can also be provided for coupling the processing system 100 to one or more peripheral devices, for example interface 112 could be a PCI card or PC card. At least one database storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, and the like.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which various embodiments of the invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments of the present invention can be implemented with numerous other general-purpose or special-purpose computing devices, systems or configurations. Examples of well-known computing systems, environments, and configurations suitable for use in embodiment of the invention include personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Various embodiments of the invention will be described herein in a general context of computer-executable instructions, such as program modules, being executed by a computer. Generally, program modules include routines, programs, objects, components, data structures, etc., that perform particular tasks or implement particular abstract data types. In certain embodiments, distributed computing environments where tasks are performed by remote processing devices that are linked through a communications network may also be employed. In distributed computing environments, program modules may be located in both local and remote computer storage media including memory storage devices.

With the general computing system environment 100 of FIG. 1 being shown and discussed above, the following description and remaining figures pertain to various exemplified embodiments of the present invention generally relating to methods for systems and methods for procedural analysis of stimulus-input patterns in user testing data to assess and validate one or more performance metrics associated with a program code build. In general, the methods described herein involve presenting, with a computing device, a testing instance of a software build to a user, the software build comprising at least one test feature configured to present one or more computerized stimuli or interaction to the user via a graphical user interface; receiving, with the computing device, one or more user inputs in response to the one or more computerized stimuli or interaction, the one or more user inputs comprising user activity data; receiving, with a processor communicably engaged with the computing device, the user activity data; processing, with the processor, the user activity data according to at least one classification model to classify the activity data, the at least one classification model being configured to classify one or more variables associated with a targeted stimulus-response pattern; analyzing a stimulus-input pattern between the user activity data and the one or more computerized stimuli or interactions to determine one or more performance metrics for the software build, the one or more performance metrics comprising a measure of efficacy of the at least one test feature; and evaluating the software build according to the one or more performance metrics to determine a pass/fail status of the software build according to a minimum performance threshold.

Figure 2:
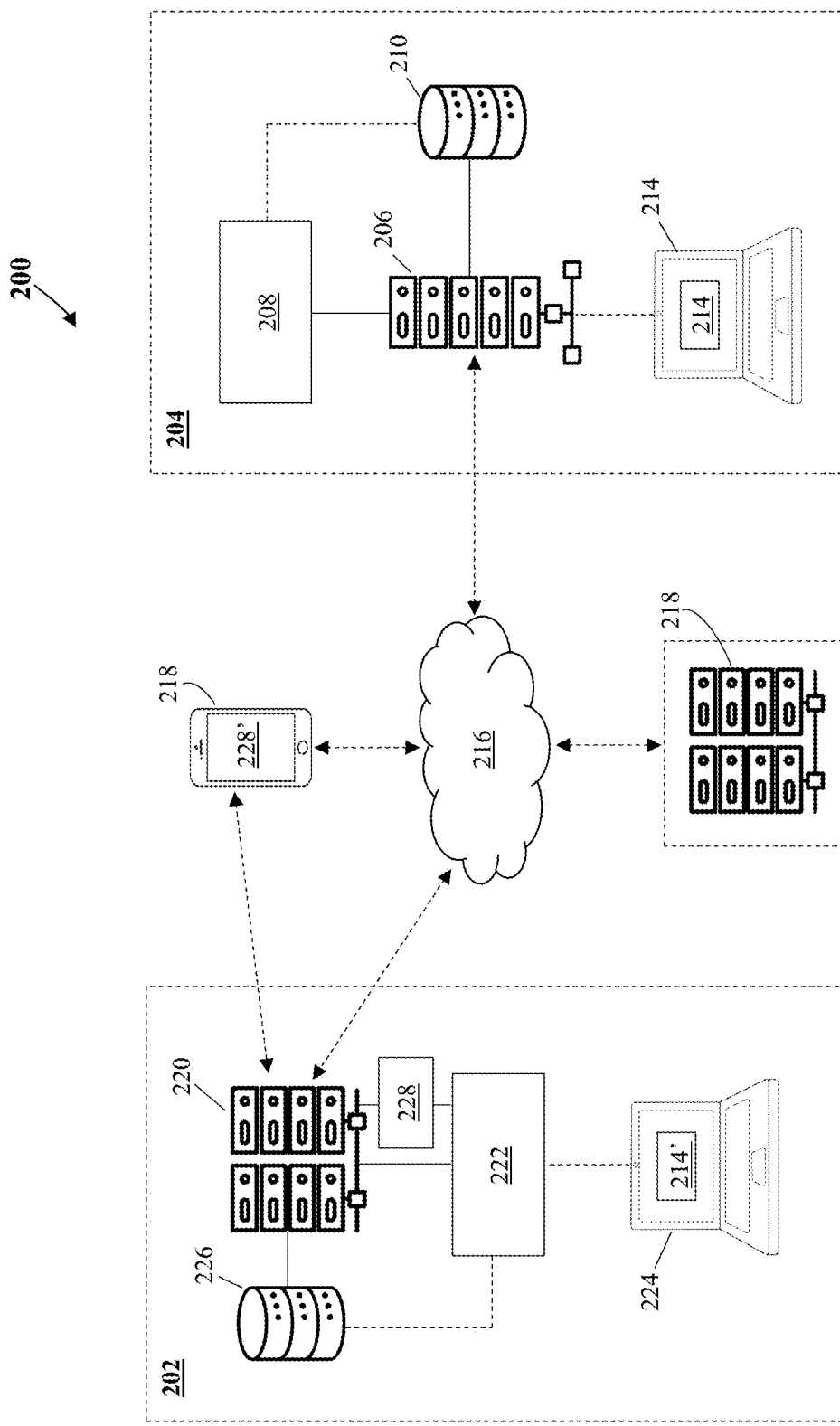
FIG. 2 is an architecture diagram of a software design control system, in accordance with certain aspects of the present disclosure.

Referring now to FIG. 2, an architecture diagram of a software design control system 200 is shown. In accordance with certain aspects of the present disclosure, system 200 comprises a software development subsystem 202 and a design control subsystem 204. Software development subsystem 202 and design control subsystem 204 may be communicably engaged through a communications network 216 (e.g. the Internet). In certain embodiments, software development subsystem 202 and design control subsystem 204 may be configured as independent systems being communicably engaged through an application programming interface or other data transfer protocol. In other embodiments, software development subsystem 202 and design control subsystem 204 may be related subsystems within a larger integrated system. For example, software development subsystem 202 and design control subsystem 204 may be related components (sequential or non-sequential) of a development operations (DevOps) toolchain. In accordance with various aspects of the present disclosure, software development subsystem 202 and design control subsystem 204 may be configured as separate software modules executing on the same server; or, software development subsystem 202 and design control subsystem 204 may be configured as separate software modules executing on the different servers within a local computing environment (i.e. LAN); or, software development subsystem 202 and design control subsystem 204 may be configured as separate software modules executing on the different servers across a distributed computing environment (i.e. WAN). In certain embodiments, software development subsystem 202 and design control subsystem 204 may be operably engaged via one or more third-party server 218. For example, third-party server 218 may comprise a cloud repository to which program code associated with a software program may be remotely stored within a software development environment. The cloud repository may comprise a versioning platform, such as GITHUB® or BITBUCKET®; and may further comprise a cloud storage and/or computing environment, such as those available from AMAZON WEB SERVICES®. In certain embodiments, third-party server 218 may provide one or more services, data, and/or processing functions to software development subsystem 202 and/or design control subsystem 204 (for example, design control module 208 and/or software development module 222 may be executed, in whole or in part, on third-party server 218).

In accordance with certain embodiments, software development subsystem 202 may be defined as a software development environment for developing at least one software program 228. In certain embodiments, software program 228 is configured as a DHI or SaMD product. Software development subsystem 202 may comprise at least one developer workstation 224 configured to execute one or more workstation application 228, at least one local and/or remote server 220 comprising one or more software development module 222, and at least one database 226 communicably engaged with server 220 and one or more software development module 222. Design control subsystem 204 may be comprised of a design control server 206, a design control module 208 executing on design control server 206, a design control database 210 communicably engaged with design control server 206 and design control module 208, and a design control workstation 214. In certain embodiments, design control workstation 214 may be configured to execute an instance of a design control application 214; and developer workstation 224 may be configured to execute an instance of a design control application 214'.

In accordance with certain embodiments, software development subsystem 202 and design control subsystem 204 may be operably engaged to define one or more deployment environments or tiers associated with software program 228. Certain exemplary deployment environments or tiers in which software development subsystem 202 and design control subsystem 204 may be operably engaged to develop, deploy, and/or execute one or more aspects of software program 228 may comprise any combination of environments or tiers as shown and described in Table 1.

TABLE 1

Environments/Tiers

| Environment/Tier | Description |
| --- | --- |
| Local Development/Trunk | Developer's machine/workstation Development server acting as a sandbox where unit testing may be performed by the developer |
| Integration | Continuous integration build target, or for developer testing of side effects |
| Testing/Test/QC/Internal Acceptance | The environment where interface testing is performed. A quality control team may ensure that the new code will not have any impact on existing functionality and may test major functionalities of the software after deploying the new code in the test environment. |
| Staging/Stage/Model/Pre-production/External-Client Acceptance/Demo | Mirror of production environment |
| Production/Live | Serves end-users/clients |

In accordance with certain embodiments, system 200 may further comprise a user device 218 being communicably engaged with server 220 to execute an instance 228' of software program 228. Instance 228' may comprise an instance of software program 228 being associated with one or more development tiers, as shown and described in Table 1. For example, instance 228' may be configured as a testing instance of software program 228. In certain embodiments, user device 218 may be configured as an end user device (i.e. external user); and in other embodiments, user device 218 may be configured as a developer user device (i.e. internal user). User device 218 may include one or more computing devices being operable to execute a software program including, but not limited to, a smartphone, a tablet computer, a wearable electronic device (e.g. a smartwatch), a laptop computer, and the like. User device 218 may be communicably engaged with one or more of server 220, third-party server 218 and/or design control server 206 via communications network 216.

Figure 3:
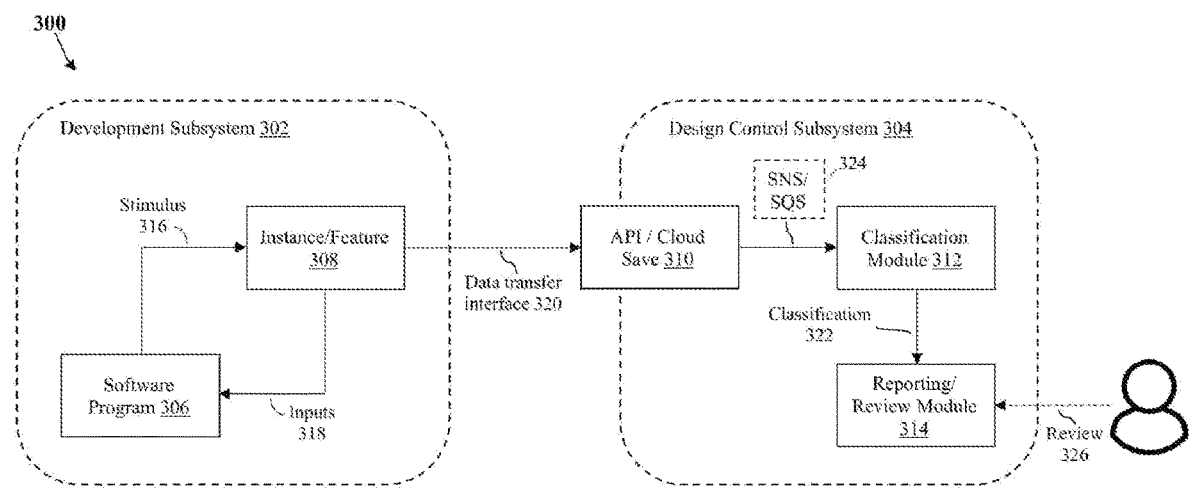
FIG. 3 is a functional block diagram of a software design control system, in accordance with certain aspects of the present disclosure.

Referring now to FIG. 3, a functional block diagram of a software design control system 300 is shown. In accordance with certain aspects of the present disclosure, system 300 may comprise development subsystem 302 and design control subsystem 304. In certain embodiments, development subsystem 302 and design control subsystem 304 may be configured as software development subsystem 202 and design control subsystem 204, as shown and described in FIG. 2. In accordance with certain embodiments, system 300 is operably configured to receive, process and analyze stimulus-response patterns in user activity data to assess the efficacy, safety, and/or performance of one or more features of a software product. In certain embodiments, the software product is configured as a DHI or SaMD.

In accordance with certain embodiments, development subsystem 302 may be configured to execute an instance 308 of software program 306 within one or more development tier. In certain embodiments, the development tier is a testing tier or pre-production tier. In other embodiments, the development tier is a production tier or live tier. In embodiments where the development tier is a testing tier or pre-production tier, software program 306 may comprise a build of a version or subversion of a software product that has yet to be deployed to a production tier or live tier. Development subsystem 302 may be configured to receive user activity data associated with one or more instance 308 of software program 306. In certain embodiments, software program 306 comprises at least one engine/algorithm being configured according to at least one clinically validated stimulus-response pattern. In certain embodiments, the at least one clinically validated stimulus-response pattern may comprise a therapeutic mechanism of action for treating or targeting one or more neurological, psychological and/or somatic conditions. Software program 306 may be configured to provide a stimulus 316 comprising one or more CSIs within an instance 308 of software program 306 executing on a user device. In accordance with certain embodiments, stimulus 316 may comprise one or more test feature(s) or incremental design change(s) being embodied within the one or more CSIs and/or one or more graphical user interface element of instance 308. Instance 308 may be configured to receive one or more user inputs 318 in response to stimulus 316 and provide inputs to software program 306. Software program 306 may provide one or more stimuli 316 and receive one or more inputs 318 via instance 308 to comprise at least one session of software program 306 within one or more development tier. In an embodiment, the at least one session may comprise a testing session. The one or more stimuli 316 and inputs 318 presented and received within the at least one session of software program 306 may comprise a plurality of user activity data.

Still referring to FIG. 3, user activity data from design control subsystem 304 may be communicated, in real-time or via a batch processing protocol, to design control subsystem 304 via data transfer interface 320. Data transfer interface 320 may comprise a network communications protocol for an application programming interface (API) 310. In certain embodiments, data transfer interface 320 may also comprise a server push for a cloud save 310 of user activity data in one or more database (e.g., design control database 210 as shown in FIG. 2). Design control subsystem 304 may be configured to communicate user activity data to classification module 312 for processing. In certain embodiments, classification module 312 may, optionally, be communicably engaged with one or more database being configured to store user activity data via cloud save 310 through a simple notification service/simple queue service 324. Simple notification service/simple queue service 324 may be configured as a publish/subscribe model between classification module 312 and the one or more database being configured to store user activity data via cloud save 310. Classification module 312 may be configured to execute one or more classification algorithms configured to process and classify the user activity data according to at least one classifier model. In certain embodiments, classification module 312 may be configured as a procedural reflection of the at least one engine/algorithm of software program 306. The at least one classifier model of classification module 312 may be configured to classify one or more variables associated with the at least one clinically validated stimulus-response pattern. In certain embodiments, the at least one classifier model of classification module 312 is configured to classify one or more variables associated with a clinically validated stimulus-response pattern for treating or targeting the one or more neurological, psychological and/or somatic conditions. The classification model may be configured as a machine learning framework comprising an ensemble learning model and/or a supervised learning model. An ensemble learning model may comprise two or more algorithms configured to analyze two or more respective variables, or metrics, within instance 308. For example, an ensemble learning framework may comprise a procedural algorithm to analyze a safety metric within user data (e.g., whether the user is in a moving car) and a classifier algorithm to analyze an efficacy metric (e.g., whether one or more stimulus-input patterns are reflective of an expected result). In certain embodiments, the classification model may comprise a random forest algorithm and/or a random decision forest algorithm. In said embodiments, one or more features of software program 306 may be represented as node(s) in the random forest algorithm or the random decision forest algorithm. Classification module 312 may be configured to process the user activity data according to the classification model to classify 322 one or more variables within the user activity data. In accordance with certain embodiments, the one or more variables may comprise one or more stimulus-input patterns between the user activity data and the one or more computerized stimuli or interactions. For example, a feature of software program 306 may include a certain type or category of CSI, such as a target discrimination stimulus or visuomotor tracking task. In accordance with such embodiments, a target discrimination stimulus (i.e., feature A) may be configured to prompt a first type of user response (i.e., input-type A) and a visuomotor tracking task (i.e., feature B) might be configured to prompt a second type of user response (i.e., input-type B) within instance 308. Classification module 312 may be configured to enable a developer user to configure feature A and feature B as nodes in the classification model and input-type A and input-type B as variables associated with a targeted (i.e., expected) stimulus-response pattern. Classification module 312 may be further configured to receive user activity data from one or more prior instances of software program 306 and process the data to generate a one training dataset for the classification model.

In accordance with certain embodiments, design control subsystem 304 may provide the output of classification module 312 to a reporting module 314. Reporting/review module 314 may be configured to process the output of classification module 312 to generate one or more performance metrics for software program 306. In certain embodiments, reporting/review module 314 may be configured to analyze the stimulus-input pattern between the user activity data and the one or more computerized stimuli or interactions to determine one or more performance metrics for software program 306. The one or more performance metrics may comprise a quantified measure of the one or more variables associated with a clinically validated stimulus-response pattern for treating or targeting the one or more neurological, psychological and/or somatic conditions in a user. In certain embodiments, the one or more performance metrics may comprise a qualitative or quantitative measure of safety, efficacy, and/or performance of at least one test feature or incremental design change for software program 306. Reporting module 314 may be further configured to process the output of classification module 312 to analyze the performance metrics and/or determine a pass/fail status of software program 306 according to a minimum performance threshold. In certain embodiments, the minimum performance threshold is a minimum degree of model fit between the actual stimulus-response pattern(s) represented in the user activity data and the expected (e.g., clinically validated) stimulus-response pattern(s) for treating or targeting the one or more neurological, psychological and/or somatic conditions. The minimum performance threshold may further comprise a minimum measure of therapeutic activity delivered to the user in response to instance 308 of software program 306 and/or a minimum amount of therapeutic activity delivered to the user on a per feature (e.g., per CSI) basis. Reporting module 314 may be further configured to render a graphical user interface comprising one or more data visualization and/or data query capabilities configured to enable a developer user to perform a review 326 for software program 306. Review 326 may be associated with one or more software development processes including, but not limited to, software/feature design, requirements analysis, feature testing, build testing, code review(s), source code control, quality control/assurance, software configuration management, testing, release management, product integration, and the like. In accordance with certain embodiments, a developer user may analyze one or more safety, efficacy and/or performance metrics for software program 306 in order to evaluate a pass/fail status for one or more test feature(s) or incremental design change(s) for instance 308. In accordance with certain embodiments, the pass/fail status may comprise a minimum net therapeutic effect threshold. The minimum net therapeutic effect threshold may define a minimum amount of therapeutic activity delivered to the user within instance 308. Reporting/review module 314 may be configured to calculate a minimum net therapeutic effect based on the total number of instances within the user activity data in which an actual stimulus-input pattern was reflective of an expected stimulus-input pattern on a per CSI basis and in the aggregate for instance 308.

Figure 4:
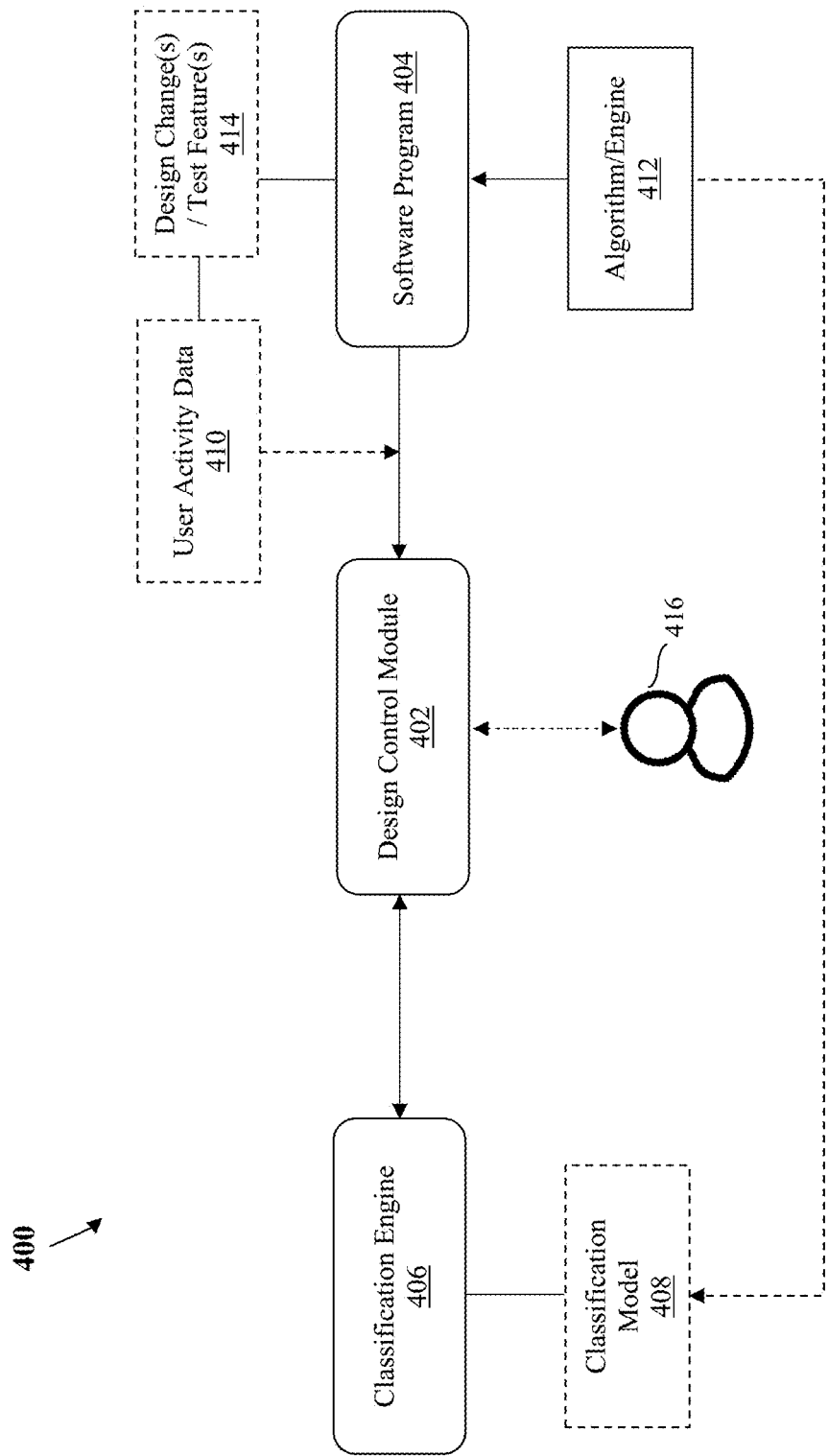
FIG. 4 is a functional block diagram of a software design control system, in accordance with certain aspects of the present disclosure.

Referring now to FIG. 4, a functional block diagram of a software design control system 400 is shown. In accordance with certain aspects of the present disclosure, a software design control module 402 may comprise a component of a DevOps toolchain. Software design control system 400 may be incorporated within one or more aspects of system 200 of FIG. 2 and/or system 300 of FIG. 3. System 400 may comprise a design control module 402 configured to enable a developer user 416 to analyze and validate one or more safety, efficacy, and performance aspects for one or more design changes and/or test features of a software program/product 404. In certain embodiments, the software program/product comprises a DHI or SaMD product. Design control module 402 may comprise a classification engine 406 and/or input from a classification engine 406. Classification engine 406 may comprise a classification model 408 representing a procedural reflection of at least one algorithm 412. Classification engine 406 may configure or select classification model 408 in response to algorithm 412. Algorithm 412 may correspond to at least one clinically validated stimulus-response pattern. Algorithm 412 may serve the basis of at least one processing engine for software program 404. Design control module 402 may receive user activity data 410 in response to an instance 414 of software program 404 having one or more design changes or test features. In certain embodiments, instance 414 comprises a version of software program 404 being executed in a development tier other than production/live tier (e.g. a testing tier or pre-production tier). In accordance with an embodiment, design control module 402 receives user activity data 410 and provides it to classification engine 406. Classification engine 406 processes user activity data 410 to determine and identify one or more variables being reflective of the clinically validated stimulus-response pattern of algorithm 412. Design control module 402 processes the output of classification engine 406 to determine one or more performance metrics for the design change(s) and/or test feature(s) 414. Design control module 402 may provide the performance metrics, as well as other data visualizations corresponding to the user activity data and/or the classification model, to developer user 416. Developer user 416 may review the performance metrics to determine the impact of design change(s) and/or test feature(s) 414 on one or more safety, efficacy and/or performance aspects of software program 404.

Figure 5:
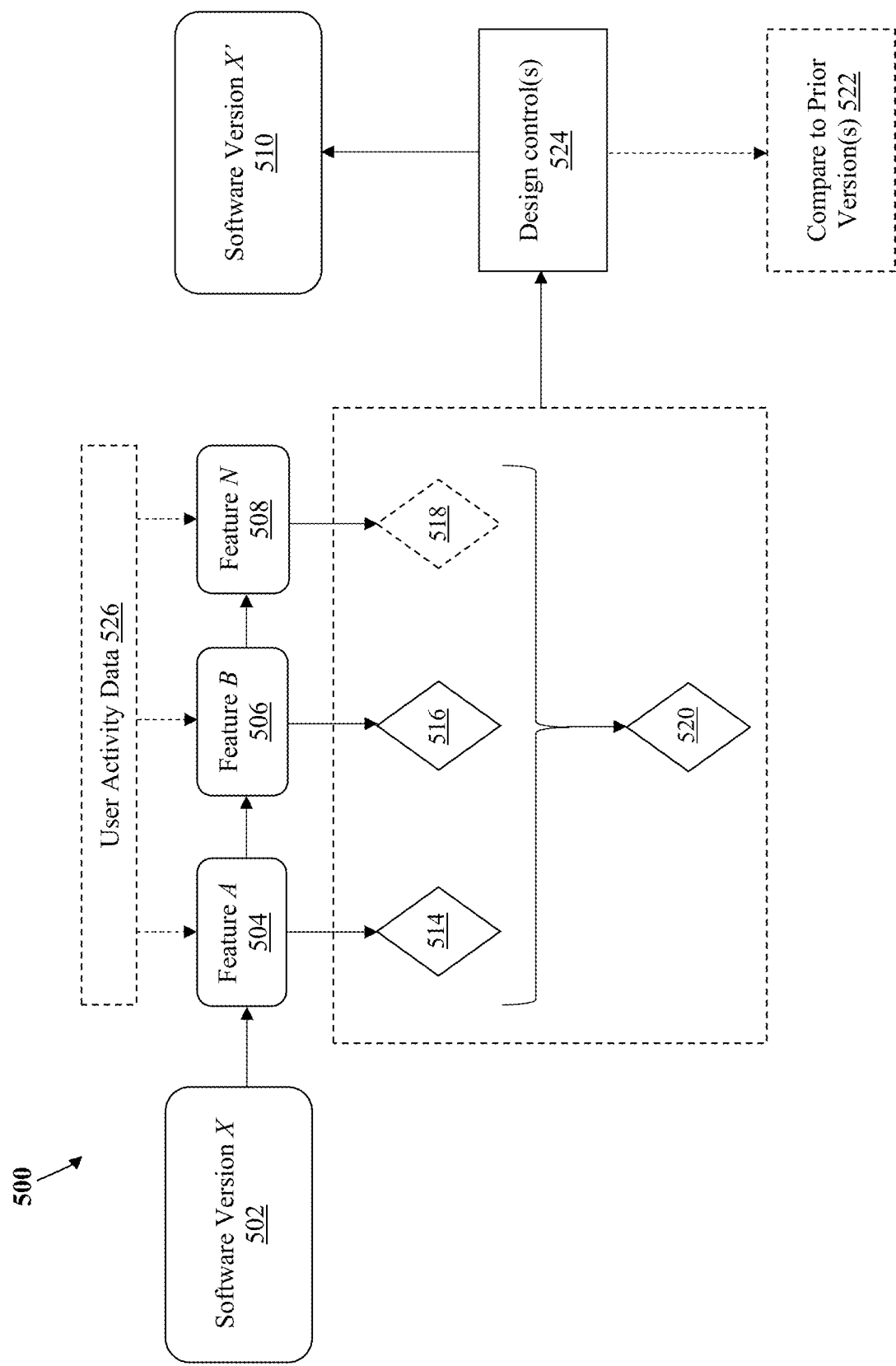
FIG. 5 is a functional block diagram of a software design control system, in accordance with certain aspects of the present disclosure.

Referring now to FIG. 5, a functional block diagram of a software design control process 500 is shown. In accordance with certain aspects of the present disclosure, software design control process 500 may be incorporated in a software design control system; for example, a software design control system as shown and described in any one of FIGS. 2-4. Design control process 500 may comprise steps for evaluating and verifying one or more features and/or design changes within a version of a software product within one or more development environments; for example, a testing environment and/or a pre-production environment. In accordance with an embodiment, design control process 500 may comprise presenting a software version X 502 within a design control system. Software version X 502 may comprise one or more features and/or design changes to be evaluated and verified; for example, Feature A 504, Feature B 506, and Feature N 508. User activity data 526 may be received in response to presenting each of Feature A 504, Feature B 506, and Feature N 508 to a user via an instance (e.g., a testing instance or a pre-production instance) of software version X 502. Design control process 500 may further comprise executing a classification model for each of Feature A 504, Feature B 506, and Feature N 508 to generate a classification 514, a classification 516, and a classification 518. In accordance with an embodiment, classification 514 may comprise a procedural reflection between a stimulus-response pattern of user activity data 526 and Feature A 504 and a clinically validated stimulus-response pattern. Likewise, classification 516 may comprise a procedural reflection between a stimulus-response pattern of user activity data 526 and Feature B 506 and the clinically validated stimulus-response pattern; and, classification 518 may comprise a procedural reflection between a stimulus-response pattern of user activity data 526 and Feature N 508 and the clinically validated stimulus-response pattern. In accordance with an embodiment, design control process 500 may be configured to determine the success or failure of a feature to deliver a desired stimulus-response pattern within software version X 502 based on classification of the user activity data. In an illustrative example, classification 518 denotes a failure of Feature N 508 to deliver a desired stimulus-response pattern within the user activity data 526. In accordance with an embodiment, design control process 500 may be further configured to determine the success or failure of a software version in delivering a desired stimulus-response pattern, in the aggregate, based on classification of user activity data. In an illustrative example, classification 518 denotes success of software version X 502 in delivering a desired stimulus-response pattern within the user activity data 526. Design control process 500 may be further configured to process one or more of classifications 514, 516, 518, 520 to executed one or more design controls 524. In accordance with an embodiment, design controls 524 may comprise rejecting one or more non-conforming features and/or design changes (e.g., Feature N 508) through one or more software quality assurance processes. In accordance with certain embodiments, design controls 524 may comprise calculating one or more performance metrics for software version X 502 based on one or more of classifications 514, 516, 518, 520. Design controls 524 may, optionally, be further configured to compare one or more performance metrics associated with software version X 502 with performance metrics associated with one or more prior versions 522. Design control process 500 may be further configured to accept or reject one or more of Feature A 504, Feature B 506, and/or Feature N 508 to define software version X' 510.

Figure 6:
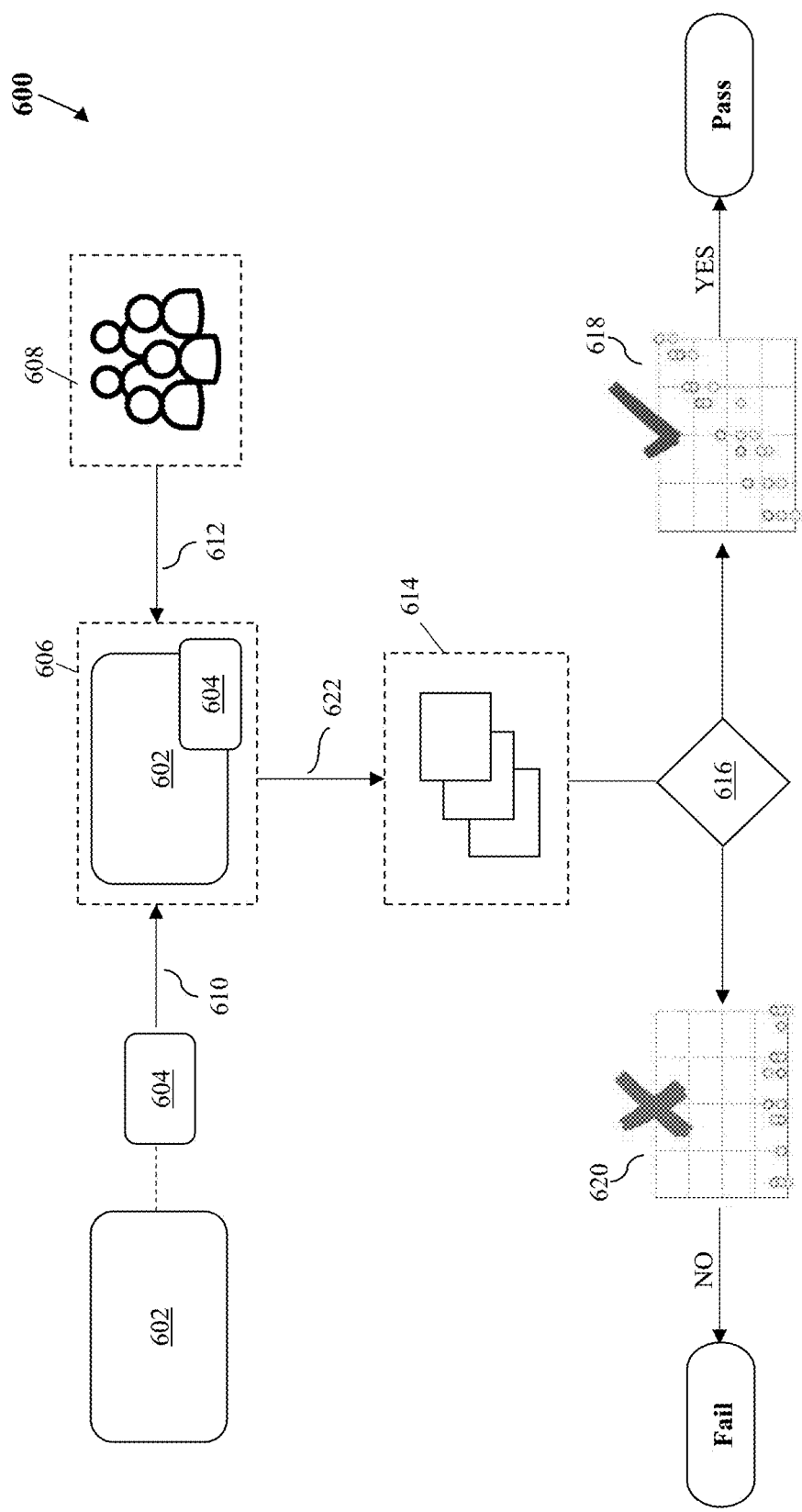
FIG. 6 is a process flow diagram of a system and method for software design control and quality assurance, in accordance with certain aspects of the present disclosure.

Referring now to FIG. 6, a process flow diagram of a software validation process 600 is shown. In accordance with certain aspects of the present disclosure, software validation process 600 may be incorporated in a software design control system; for example, a software design control system as shown and described in any one of FIGS. 2-4. In accordance with an embodiment, software validation process 600 comprises a software program 602 comprising at least one new feature or design change 604 being deployed 610 within a development environment 606. One or more users 608 may execute an instance 612 of software program 602 comprising at least one new feature or design change 604. User activity data 622 may be processed according to a classification model 614. Classification model 614 may be configured to classify one or more variables associated with a clinically validated stimulus-response pattern. Software validation process 600 may be further configured to evaluate 616 whether user activity data 622 reflects a desired stimulus-response pattern 618 or fails to reflect a desired stimulus-response pattern 620. If user activity data 622 fails to reflect a desired stimulus-response pattern 620 according to classification 614, software validation process 600 may be configured to assign a FAIL status to feature or design change 604. If user activity data 622 reflects a desired stimulus-response pattern 618 according to classification 614, software validation process 600 may be configured to assign a PASS status to feature or design change 604.

Figure 7:
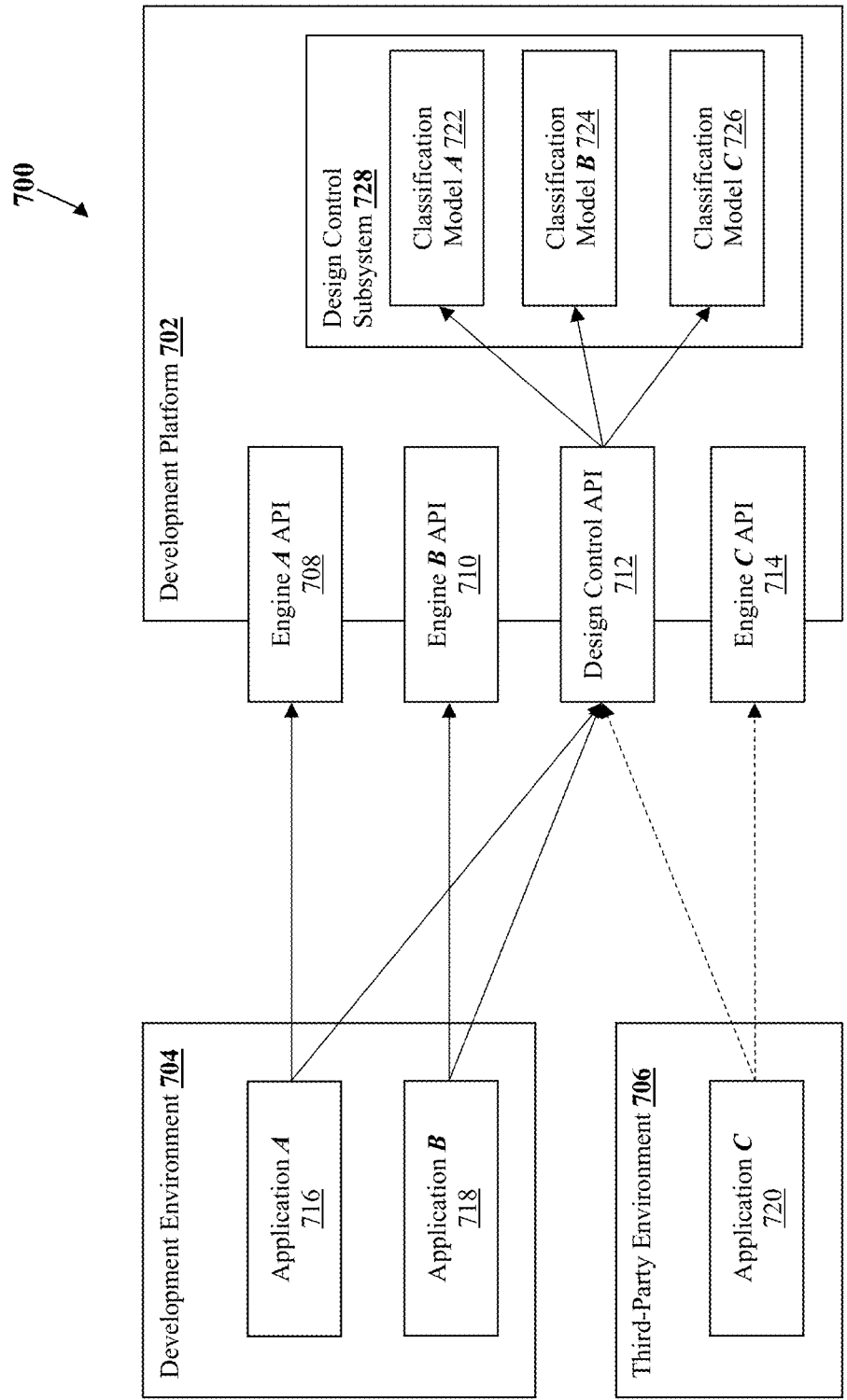
FIG. 7 is a functional block diagram of a software design control system, in accordance with certain aspects of the present disclosure.

Referring now to FIG. 7, a functional block diagram of a software design control system 700 is shown. In accordance with certain aspects of the present disclosure, a development platform 702 may be communicably engaged with a development environment 704 and a third-party environment 706 via one or more APIs. In accordance with certain embodiments, development environment 704 may comprise source code for an application A 716 and an application B 718. In certain embodiments, third-party environment 706 may comprise source code for an application C 720. In certain embodiments, application A 716 may be communicably engaged with an Engine A API 708 to configure one or more CSIs within application A 716. Likewise, application B 718 may be communicably engaged with an Engine B API 710 to configure one or more CSIs within application B 718; and, application C 720 may be communicably engaged with an Engine C API 714 to configure one or more CSIs within application C 720. Application A 716, Application B 718 and/or Application C 720 may be communicably engaged with design control API 712 to provide user activity data and application data to design control subsystem 728. Design control subsystem 728 may be configured to process user activity data and application data according to one or more classification model(s). In accordance with an illustrative example, design control subsystem 728 is configured to execute a classification model A 722 to classify user activity data associated with Application A 716; a classification model B 724 to classify user activity data associated with Application B 718; and a classification model C 726 to classify user activity data associated with Application C 720. In accordance with certain embodiments, design control subsystem 728 comprises a tool in a DevOps toolkit within development environment 704 and/or third-party environment 706.

Figure 8:
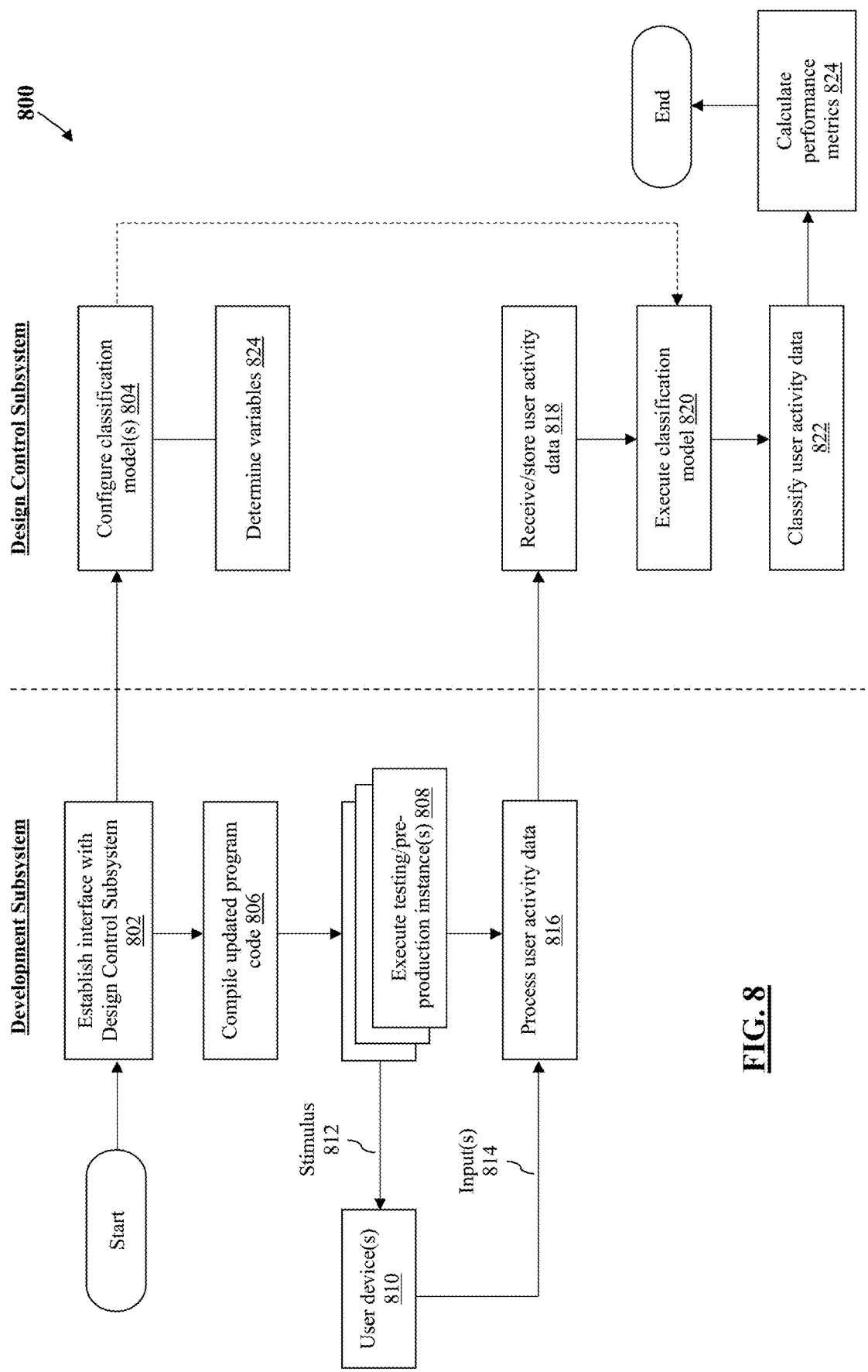
FIG. 8 is a functional block diagram of a routine for classifying user activity data within a software design control system, in accordance with certain aspects of the present disclosure.

Referring now to FIG. 8, a functional block diagram of a routine 800 for classifying user activity data within a software design control system is shown. In accordance with certain aspects of the present disclosure, routine 800 may be incorporated in a software design control system as shown and described in any one of FIGS. 2-4. Routine 800 may comprise one or more steps being executed between a development subsystem and a design control subsystem; for example, development subsystems 202 and/or 302 and design control subsystems 204 and/or 304 (as shown and described in FIGS. 2-3, respectively). In accordance with an embodiment, routine 800 may be initiated by establishing a communications interface 802 between the development subsystem and the design control subsystem. Design control subsystem may be configured to configure one or more classification model(s) 804 in response to one or more application data from development subsystem. Configuring the one or more classification model(s) 804 may further comprise determining one or more model variables 824 comprising one or more performance criteria. Routine 800 may continue by compiling updated program code 806 comprising one or more new features and/or incremental design changes. Routine 800 may continue by executing a testing or pre-production instance of the updated program code 808. The testing or pre-production instance 808 may comprise providing one or more stimulus 812 to one or more user devices 810 and receiving one or more inputs 814 in response to the one or more stimulus 812. In accordance with certain embodiments, the one or more stimulus may comprise one or more CSIs. Routine 800 may continue by processing the user activity data 816 and communicating the user activity data to the design control subsystem. Routine 800 may continue at the design control subsystem by receiving, and optionally storing, the user activity data 818. Routine 800 may continue by executing the classification model 820 (as configured in Step 804) to classify the user activity data 822. Routine 800 may conclude by processing the classified user activity data to calculate one or more performance metrics 824 associated with the updated program code. In accordance with certain embodiments, the one or more performance metrics may comprise one or more quantified measure of at least one safety, efficacy, or performance variable associated with the updated program code.

Figure 9:
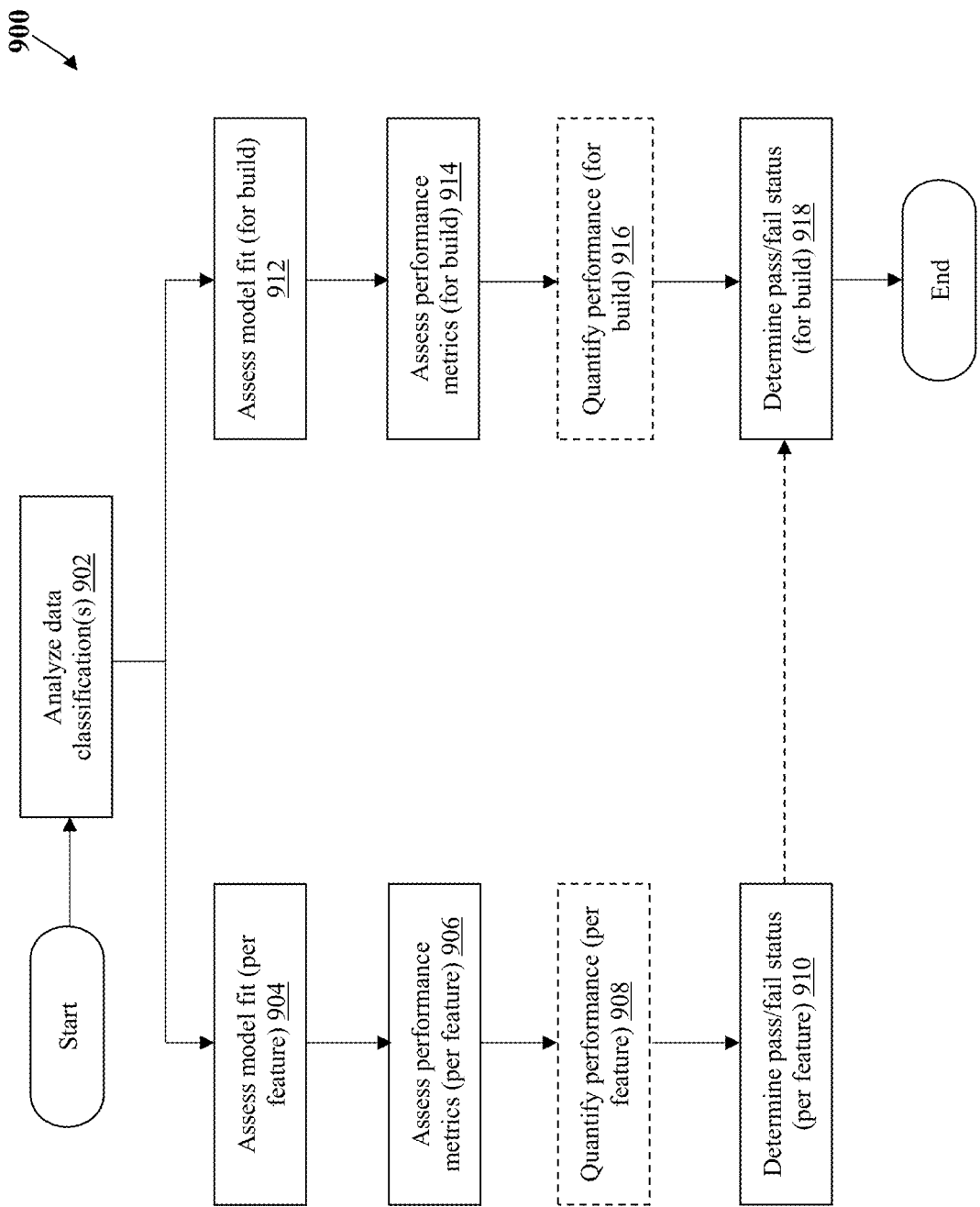
FIG. 9 is a functional block diagram of a routine for determining a pass/fail status of a software build within a software design control system, in accordance with certain aspects of the present disclosure.

Referring now to FIG. 9, a functional block diagram of a routine 900 for determining a pass/fail status of a software build within a software design control system is shown. In accordance with certain aspects of the present disclosure, routine 900 may be incorporated in a software design control system as shown and described in any one of FIGS. 2-4. Routine 900 may comprise one or more steps being executed between a development subsystem and a design control subsystem; for example, development subsystems 202 and/or 302 and design control subsystems 204 and/or 304 (as shown and described in FIGS. 2-3, respectively). In certain embodiments, routine 900 may comprise a continuation of one or more steps of routine 800 (as shown and described in FIG. 8).

Routine 900 may comprise analyzing data classification (s) 902 corresponding to executing one or more data model for user activity data associated with an instance of a software program. In accordance with certain embodiments, Step 902 may comprise one or more Substeps 904-910 and/or 912-918. In certain embodiments, Substeps 904-910 may include the steps of assessing model fit for the classification model (on a per feature basis) 904; assessing one or more performance metrics for the version of the software program (on a per feature basis) 906; quantifying one or more performance metrics for the version of the software program (on a per feature basis) 908; and determining at least one pass/fail status for the version of the software program (on a per feature basis) 910. In certain embodiments, Substeps 912-918 may include the steps of assessing model fit for the classification model (for the current build/version) 912; assessing one or more performance metrics for the version of the software program (for the current build/version) 914; quantifying one or more performance metrics for the version of the software program (for the current build/version) 916; and determining at least one pass/fail status for the version of the software program (for the current build/version) 918.

Figure 10:
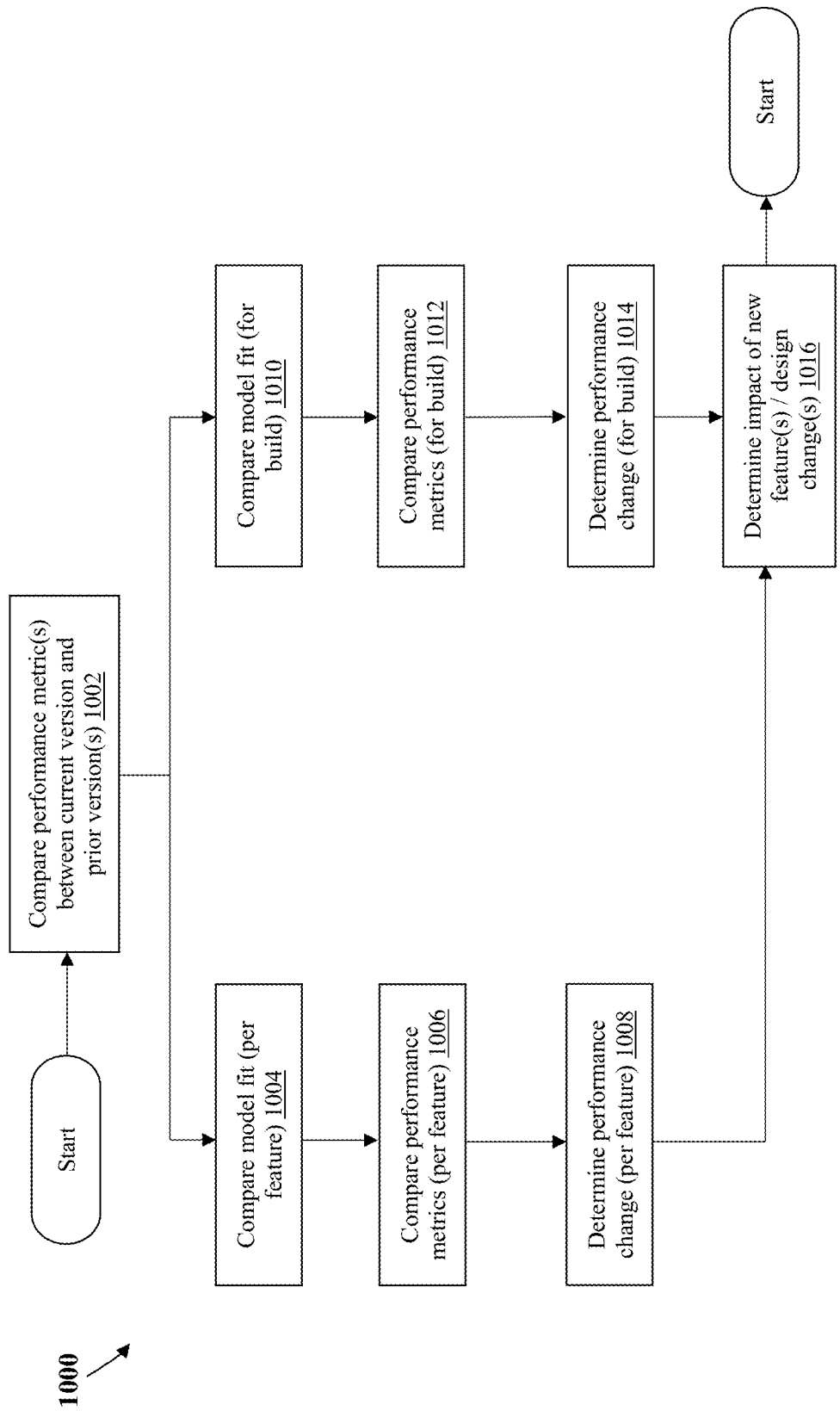
FIG. 10 is a functional block diagram of a routine for determining the impact of a design change within a software design control system, in accordance with certain aspects of the present disclosure.

Referring now to FIG. 10, a functional block diagram of a routine 1000 for determining the impact of a design change within a software design control system is shown. In accordance with certain aspects of the present disclosure, routine 1000 may be incorporated in a software design control system as shown and described in any one of FIGS. 2-4. Routine 1000 may comprise one or more steps being executed between a development subsystem and a design control subsystem; for example, development subsystems 202 and/or 302 and design control subsystems 204 and/or 304 (as shown and described in FIGS. 2-3, respectively). In certain embodiments, routine 1000 may comprise a continuation of one or more steps of routine 800 and/or routine 900 (as shown and described in FIGS. 8-9).

Routine 1000 may comprise comparing one or more performance metrics between a current version of a software program and at least one prior version of the software program 1002. In accordance with certain embodiments, Step 1002 may comprise one or more Substeps 1004-1008 and/or 1010-1014. In certain embodiments, Substeps 1004-1008 may include the steps of comparing model fit for the classification model between the current version of a software program and at least one prior version of the software program (on a per feature basis) 1004; comparing one or more performance metrics between the current version of a software program and at least one prior version of the software program (on a per feature basis) 1006; and determining one or more change in performance between the current version of the software program and at least one prior version of the software program (on a per feature basis) 1008. In certain embodiments, Substeps 1010-1014 may include the steps of comparing model fit for the classification model between the current version of a software program and at least one prior version of the software program (for the current build/version) 1010; comparing one or more performance metrics between the current version of a software program and at least one prior version of the software program (for the current build/version) 1012; and determining one or more change in performance between the current version of the software program and at least one prior version of the software program (for the current build/version) 1014. In accordance with certain embodiments, routine 1000 may conclude by determining a quantitative and/or qualitative measure of impact of the new features and/or design changes on the software program 1016, as compared between a current version of the software program and one or more prior versions of the software program.

Figure 11:
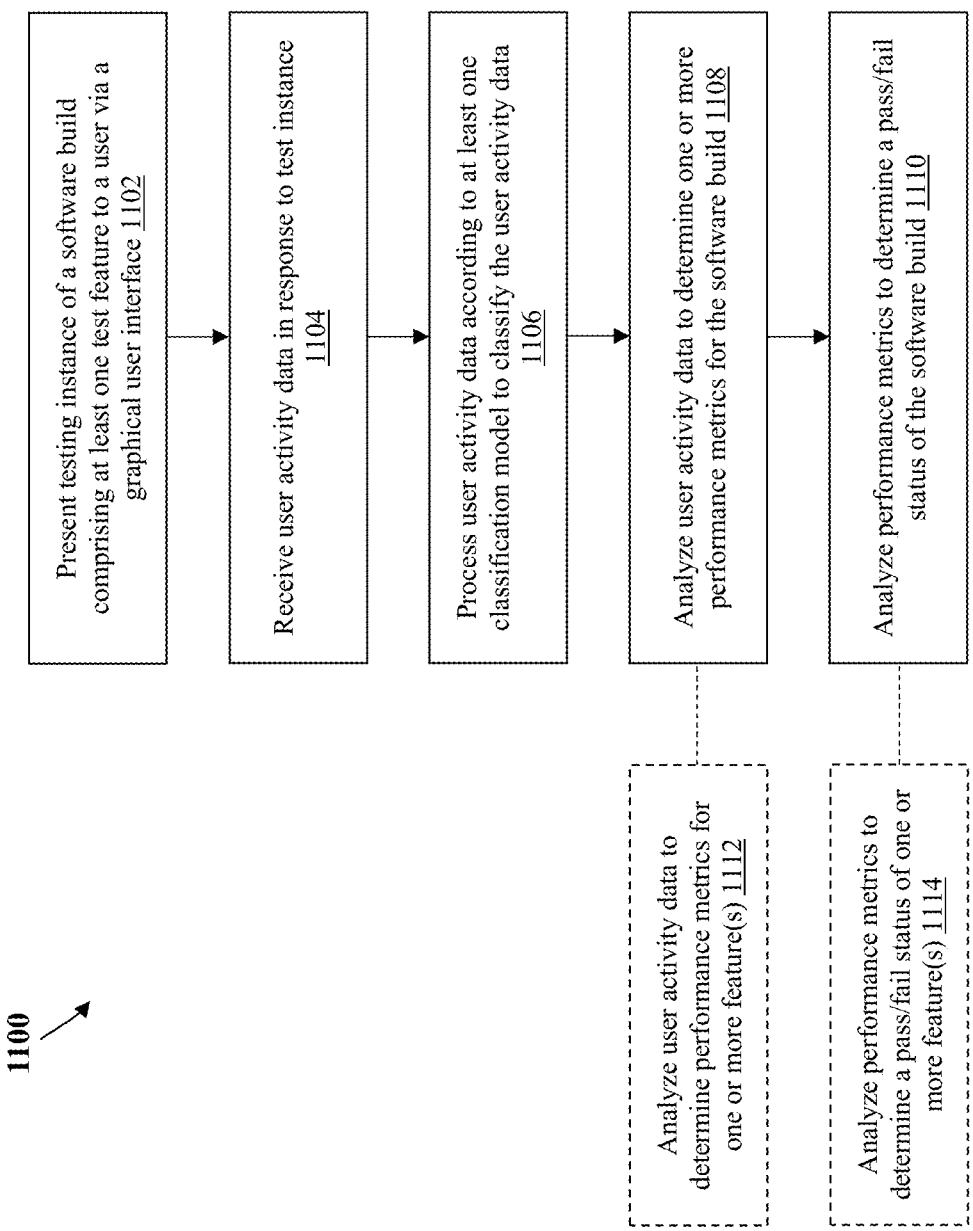
FIG. 11 is a process flow diagram of a method for software design control and quality assurance, in accordance with certain aspects of the present disclosure.

Referring now to FIG. 11, a process flow diagram of a method 1100 for software design control and quality assurance is shown. In accordance with certain embodiments, the software program is configured as a DHI or SaMD product. In accordance with certain aspects of the present disclosure, one or more steps of method 1100 may be incorporated in, and/or embodied by, one or more system, processes and/or routines and shown and described in FIGS. 1-10. Method 1100 may comprise one or more steps being executed between a development subsystem and a design control subsystem; for example, development subsystems 202 and/or 302 and design control subsystems 204 and/or 304 (as shown and described in FIGS. 2-3, respectively). In accordance with an embodiment, method 1100 may comprise presenting a testing instance of a software build comprising at least one test feature or design change to a user via a graphical user interface 1102. Method 1100 may further comprise receiving user activity data from one or more users 1104 in response to presenting the testing instance via the graphical user interface. Method 1100 may further comprise processing the user activity data according to at least one classification model to classify the user activity data 1106. Method 1100 may further comprise analyzing the user activity data to determine one or more performance metrics for the software build 1108. In certain embodiments, method 1100 may further comprise analyzing the user activity data to determine performance metrics for one or more feature(s) 1112. Method 1100 may further comprise analyzing the performance metrics to determine a pass/fail status of the software build 1110. In certain embodiments, method 1100 may further comprise analyzing the performance metrics to determine a pass/fail status of one or more feature(s) 1114.

Figure 12:
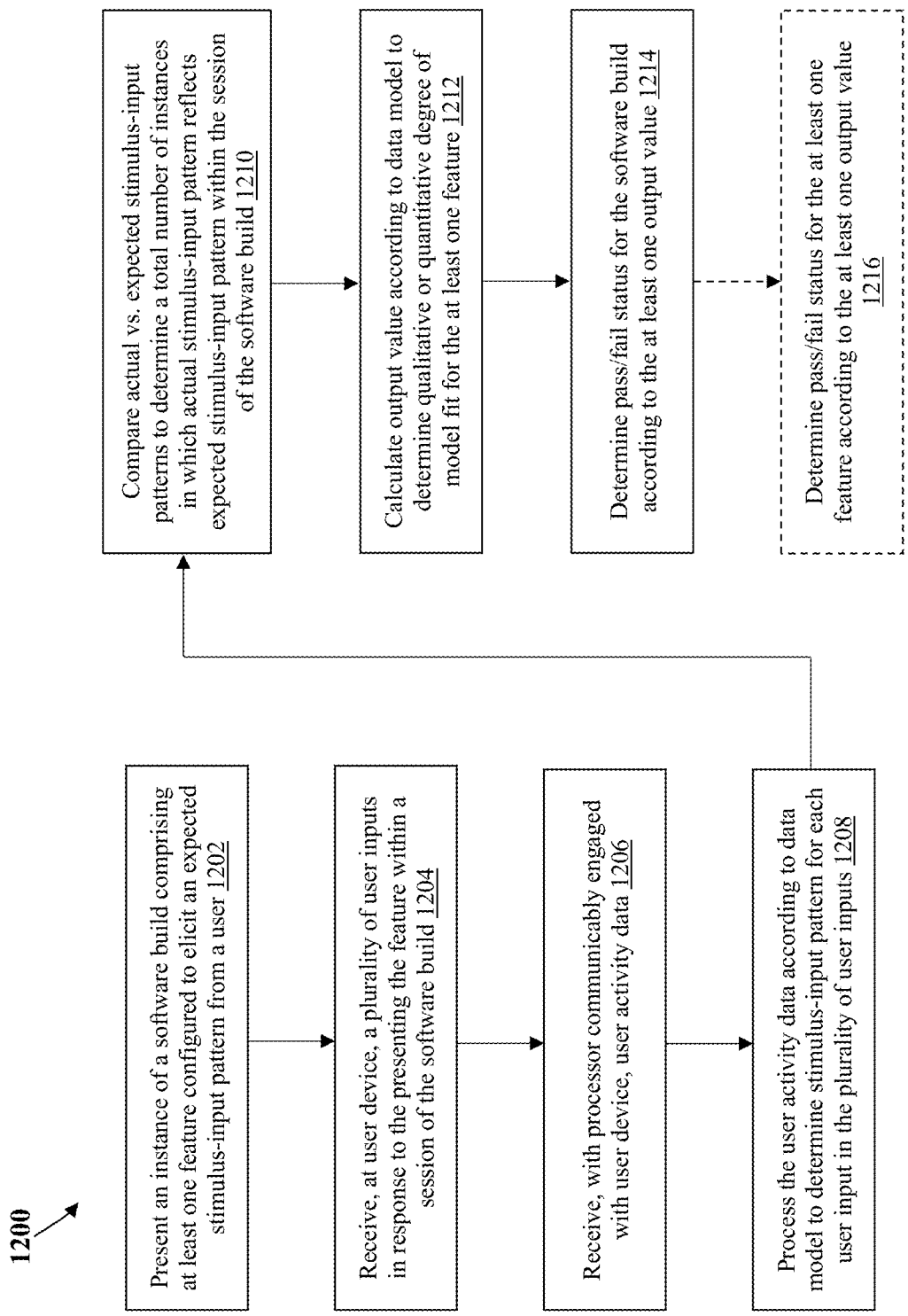
FIG. 12 is a process flow diagram of a method for software design control and quality assurance, in accordance with certain aspects of the present disclosure.

Referring now to FIG. 12, a process flow diagram of a method 1200 for software design control and quality assurance for a software program is shown. In accordance with certain embodiments, the software program is configured as a DHI or SaMD product. In accordance with certain aspects of the present disclosure, one or more steps of method 1200 may be incorporated in, and/or embodied by, one or more system, processes or routines and shown and described in FIGS. 1-10. Method 1200 may comprise one or more steps being executed between a development subsystem and a design control subsystem; for example, development subsystems 202 and/or 302 and design control subsystems 204 and/or 304 (as shown and described in FIGS. 2-3, respectively). In accordance with certain embodiments, method 1200 may comprise a continuation of, or may otherwise be incorporated within, one or more steps, or sub-steps, of method 1100 (as shown and described in FIG. 11). In accordance with certain aspects of the present disclosure, method 1200 may comprise one or more steps or operations for testing and/or software quality assurance for a DHI or SaMD product. Method 1200 may include one or more steps for presenting, with a user computing device via a graphical user interface, an instance of a software build to a user (Step 1202). In certain embodiments, the software build may comprise a testing or production instance of a software product including at least one feature configured to elicit an expected stimulus-input pattern from a user in response to presenting one or more computerized stimuli or interactions at a graphical user interface. Method 1200 may proceed by executing or performing one or more steps for receiving, via an input sensor of the user computing device, a plurality of user inputs in response to presenting the one or more computerized stimuli or interactions within the instance of the software build (Step 1204). The user activity data may be communicated and received by a local or remote processor communicably engaged with the input sensor of the user computing device (Step 1206) and may be stored in at least one non-transitory computer readable medium communicably engaged with the local or remote processor. Method 1200 may proceed by executing or performing one or more steps or sub-steps for processing, with the local or remote processor, the user activity data according to at least one data model to determine one or more actual stimulus-input pattern for each user input in the plurality of user inputs (Step 1208). In accordance with certain embodiments, the at least one data model may comprise a classification model configured to classify one or more variables associated with one or more performance, safety or efficacy parameters for the software product (e.g., the DHI or SaMD product). Method 1200 may proceed by executing one or more steps or sub-steps for comparing the one or more actual stimulus-input pattern for each user input in the plurality of user inputs to the expected stimulus-input pattern for the at least one feature to determine a total number of instances in which the one or more actual stimulus-input pattern was reflective of the expected stimulus-input pattern within the session of the software build (Step 1210). In accordance with certain embodiments, method 1200 may include one or more steps for calculating a measure of net therapeutic activity within the session of the software build according to the total number of instances in which the one or more actual stimulus-input pattern was reflective of the expected stimulus-input pattern. The one or more steps may further include one or more sub-steps for calculating a measure of active therapeutic delivery for the at least one feature within the session of the software build according to the total number of instances in which the one or more actual stimulus-input pattern was reflective of the expected stimulus-input pattern. Method 1200 may proceed by executing or performing one or more processing steps or sub-steps, with the local or remote processor, for calculating at least one output value for the user activity data according to the at least one data model (Step 1212). In accordance with certain exemplary embodiments, the at least one output value is configured to provide a qualitative or quantitative degree of model fit for the at least one feature. Method 1200 may proceed by executing or performing one or more steps or sub-steps for determining a pass/fail status for the software build according to the at least one output value (Step 1214) and/or determining a pass/fail status for the at least one feature according to the at least one output value (Step 1216). In certain embodiments, method 1200 may include one or more steps or sub-steps for comparing the at least one output value to at least one prior output value associated with at least one prior version of the software build to determine a measure of change attributable to the at least one feature.

In certain embodiments in which one or more measures of therapeutic activity/delivery within the session of the software build are measured, method 1200 may also include one or more steps for comparing the measure of net therapeutic activity within the session of the software build to at least one prior measure of net therapeutic activity associated with at least one prior version of the software build to determine a measure of change attributable to the at least one feature. In such embodiments, a pass/fail status for the software build may be determined according to a measure of net therapeutic activity within the session of the software build and/or a measure of active therapeutic delivery for the at least one feature within the session of the software build.

Figure 13:
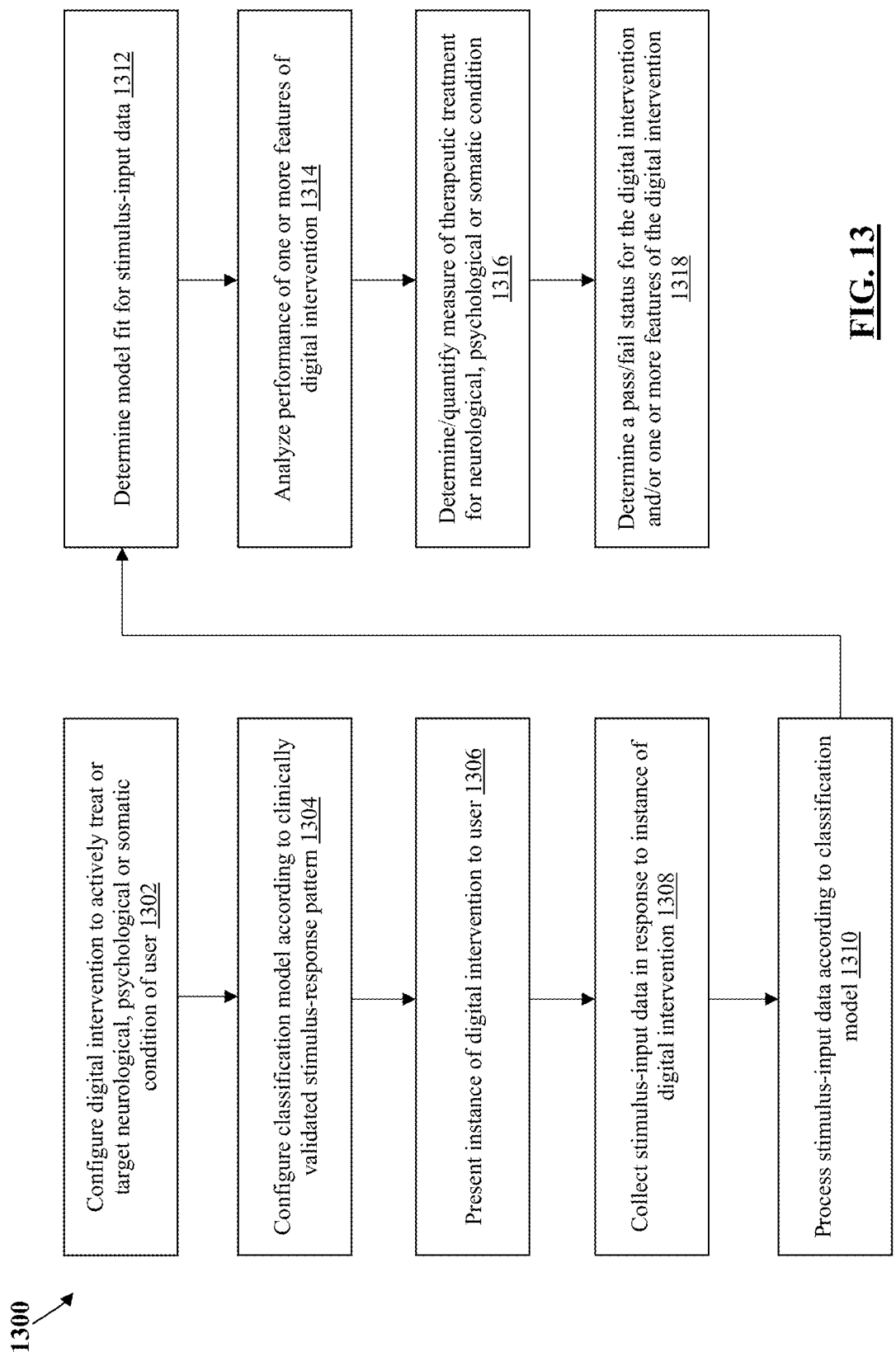
FIG. 13 is a process flow diagram of a method for software design control and quality assurance, in accordance with certain aspects of the present disclosure.

Referring now to FIG. 13, a process flow diagram of a method 1300 for software design control and quality assurance for a software program is shown. In accordance with certain embodiments, the software program is configured as a DHI or SaMD product. In accordance with certain aspects of the present disclosure, method 1300 may be incorporated in a software design control system as shown and described in any one of FIGS. 2-4. Method 1300 may comprise one or more steps being executed between a development subsystem and a design control subsystem; for example, development subsystems 202 and/or 302 and design control subsystems 204 and/or 304 (as shown and described in FIGS. 2-3, respectively). In certain embodiments, method 1300 may comprise a continuation of, or may otherwise be incorporated within, one or more steps, or sub-steps, of method 1100 (as shown and described in FIG. 11) and/or method 1200 (as shown and described in FIG. 12). In accordance with an embodiment, method 1300 may comprise configuring a digital intervention to actively treat or target neurological, psychological or somatic condition of user 1302. Method 1300 may further comprise configuring a classification model according to clinically validated stimulus-response pattern 1304. Method 1300 may further comprise presenting an instance of the digital intervention to user 1306. Method 1300 may further comprise collecting stimulus-input data in response to instance of digital intervention 1308. Method 1300 may further comprise processing stimulus-input data according to the classification model 1310. Method 1300 may further comprise determining model fit for the stimulus-input data 1312 in response to processing stimulus-input data according to the classification model to generate one or more performance metrics. In accordance with certain embodiments, the one or more performance metrics may comprise one or more quantified measure of safety, efficacy, and or performance for the digital intervention. Method 1300 may further comprise analyzing performance metrics for one or more features of the digital intervention 1314. Method 1300 may further comprise determining and/or quantifying a measure of therapeutic treatment for neurological, psychological or somatic condition 1316 associated with each of the one or more features of the digital intervention and/or the digital intervention as a whole. Method 1300 may further comprise determining a pass/fail status for each of the one or more features of the digital intervention and/or the digital intervention as a whole 1318.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions (i.e., computer-executable instructions) may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s). Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrases are used herein, a processor may be "operable to" or "configured to" perform a certain function in a variety of ways, including, for example, by having one or more general-purpose circuits perform the function by executing particular computer-executable program code embodied in computer-readable medium, and/or by having one or more application-specific circuits perform the function.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." As used herein, the terms "right," "left," "top," "bottom," "upper," "lower," "inner" and "outer" designate directions in the drawings to which reference is made.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A method for software quality assurance, comprising:
presenting, with a user computing device via a user interface, an instance of a software build to a user, wherein the software build comprises at least one feature comprising one or more computerized stimuli or interactions configured to elicit an expected stimulus-input pattern from the user in response to the one or more computerized stimuli or interactions,
wherein the expected stimulus-input pattern comprises a clinically validated stimulus-response pattern for treating or targeting one or more neurological, psychological and/or somatic condition in the user;
receiving, with at least one sensor communicably engaged with the user computing device, a plurality of user inputs in response to presenting the one or more computerized stimuli or interactions within the instance of the software build, the plurality of user inputs comprising user activity data for a session of the software build;

communicating, via a network communications protocol comprising an application programming interface, the user activity data from a first server communicably engaged with the user computing device to a second server, wherein the first server comprises a software development subsystem server and the second server comprises a design control subsystem server;

receiving, at a classification module executing on the second server, the user activity data, wherein the classification module is communicably engaged with a design control subsystem database via a simple notification service or a simple queue service, wherein the design control subsystem database is configured to store the user activity data;

processing, via the classification module, the user activity data to determine one or more actual stimulus-input patterns for each user input in the plurality of user inputs, wherein the classification module comprises a computer-implemented machine learning framework comprising an ensemble learning model or a supervised learning model configured to classify one or more variables between the user activity data and the clinically validated stimulus-response pattern, wherein the classification module is configured to calculate a degree of conformity between the one or more actual stimulus-input patterns and the clinically validated stimulus-response pattern for treating or targeting the one or more neurological, psychological and/or somatic condition in the user;

comparing, with the second server, the one or more actual stimulus-input patterns for each user input in the plurality of user inputs to the expected stimulus-input pattern for the at least one feature to determine a total number of instances in which the one or more actual stimulus-input patterns was reflective of the expected stimulus-input pattern within the session of the software build;

calculating, with the second server, at least one output value for the user activity data according to the classification module, wherein the at least one output value comprises a qualitative or quantitative degree of conformity between the one or more actual stimulus-input patterns and the expected stimulus-input pattern for the at least one feature;

calculating, with the second server, a measure of net therapeutic activity within the session of the software build according to the total number of instances in which the one or more actual stimulus-input patterns was reflective of the expected stimulus-input pattern within the session of the software build; and determining, with the second server, a pass/fail status for the software build according to the at least one output value and the measure of net therapeutic activity within the session of the software build, wherein determining the pass/fail status comprises determining a minimum performance threshold for the session of the software build, wherein the minimum performance threshold comprises a minimum degree of conformity between the one or more actual stimulus-input patterns and the clinically validated stimulus-response pattern for treating or targeting the one or more neurological, psychological and/or somatic condition in the user, and wherein the minimum performance threshold further comprises a minimum measure of therapeutic activity delivered to the user within the session of the software build.

2. The method of claim 1 further comprising calculating a measure of active therapeutic delivery for the at least one feature within the session of the software build according to the total number of instances in which the one or more actual stimulus-input patterns was reflective of the expected stimulus-input pattern.

3. The method of claim 2 further comprising comparing the measure of net therapeutic activity within the session of the software build to at least one prior measure of net therapeutic activity associated with at least one prior version of the software build to determine a measure of change attributable to the at least one feature.

4. The method of claim 2 further comprising determining the pass/fail status for the software build according to the measure of active therapeutic delivery associated with the at least one feature within the session of the software build.

5. The method of claim 1 wherein the computer-implemented machine learning framework of the classification module is configured to classify one or more variables associated with one or more performance, safety or efficacy parameters.

6. The method of claim 1 further comprising comparing the at least one output value to at least one prior output value associated with at least one prior version of the software build to determine a measure of change attributable to the at least one feature.

7. A system for software quality assurance, comprising:
a processor; and
a non-transitory computer readable storage medium communicably engaged with the processor and encoded with processor-executable instructions that, when executed, cause the processor to perform one or more operations comprising:

presenting a user interface comprising an instance of a software build to a user via a user computing device, wherein the software build comprises at least one feature comprising one or more computerized stimuli or interactions configured to elicit an expected stimulus-input pattern from the user in response to the one or more computerized stimuli or interactions, wherein the expected stimulus-input pattern comprises a clinically validated stimulus-response pattern for treating or targeting one or more neurological, psychological and/or somatic condition in the user;

receiving a plurality of user activity data for a session of the software build, wherein the plurality of user activity data comprises a plurality of user inputs in response to the one or more computerized stimuli or interactions within the instance of the software build;

communicating, via a network communications protocol comprising an application programming interface, the plurality of user activity data from a first server communicably engaged with the user computing device to a second server, wherein the first server comprises a software development subsystem server and the second server comprises a design control sub system server;

receiving, at a classification module executing on the second server, the plurality of user activity data, wherein the classification module is communicably engaged with a design control subsystem database via a simple notification service or a simple queue service, wherein the design control subsystem database is configured to store the plurality of user activity data;

processing, via the classification module executing on the second server, the plurality of user activity data to determine one or more actual stimulus-input patterns for each user input in the plurality of user inputs, wherein the classification module comprises a computer-implemented machine learning framework comprising an ensemble learning model or a supervised learning model configured to classify one or more variables between the plurality of user activity data and the clinically validated stimulus-response pattern, wherein the classification module is configured to calculate a degree of conformity between the one or more actual stimulus-input patterns and the clinically validated stimulus-response pattern for treating or targeting the one or more neurological, psychological and/or somatic condition in the user;

comparing the one or more actual stimulus-input patterns for each user input in the plurality of user inputs to the expected stimulus-input pattern for the at least one feature to determine a total number of instances in which the one or more actual stimulus-input patterns was reflective of the expected stimulus-input pattern within the session of the software build;

calculating at least one output value for the plurality of user activity data according to the classification module, wherein the at least one output value comprises a qualitative or quantitative degree of conformity between the one or more actual stimulus-input patterns and the expected stimulus-input pattern for the at least one feature;

calculating a measure of net therapeutic activity within the session of the software build according to the total number of instances in which the one or more actual stimulus-input patterns was reflective of the expected stimulus-input pattern within the session of the software build; and determining a pass/fail status for the software build according to the at least one output value and the measure of net therapeutic activity within the session of the software build, wherein determining the pass/fail status comprises determining a minimum performance threshold for the session of the software build, wherein the minimum performance threshold comprises a minimum degree of conformity between the one or more actual stimulus-input patterns and the clinically validated stimulus-response pattern for treating or targeting the one or more neurological, psychological and/or somatic condition in the user, and wherein the minimum performance threshold comprises a minimum measure of therapeutic activity delivered to the user within the session of the software build.

8. The system of claim 7 wherein the one or more operations further comprise calculating a measure of active therapeutic delivery for the at least one feature within the session of the software build according to the total number of instances in which the one or more actual stimulus-input patterns was reflective of the expected stimulus-input pattern.

9. The system of claim 8 wherein the one or more operations further comprise comparing the measure of net therapeutic activity within the session of the software build to at least one prior measure of net therapeutic activity associated with at least one prior version of the software build to determine a measure of change attributable to the at least one feature.

10. The system of claim 8 wherein the one or more operations further comprise determining the pass/fail status for the software build according to the measure of active therapeutic delivery for the at least one feature within the session of the software build.

11. The system of claim 7 wherein the computer-implemented machine learning framework of the classification module is configured to classify one or more variables associated with one or more performance, safety or efficacy parameters.

12. The system of claim 7 wherein the one or more operations further comprise comparing the at least one output value to at least one prior output value associated with at least one prior version of the software build to determine a measure of change attributable to the at least one feature.

13. The system of claim 7 wherein the one or more operations further comprise determining the pass/fail status for the software build according to at least one safety parameter associated with the one or more computerized stimuli or interactions.

14. A non-transitory computer-readable medium encoded with instructions for commanding one or more processors to execute operations for software quality assurance, the operations comprising:

presenting a user interface comprising an instance of a software build to a user via a user computing device, wherein the software build comprises at least one feature comprising one or more computerized stimuli or interactions configured to elicit an expected stimulus-input pattern from the user in response to the one or more computerized stimuli or interactions, wherein the expected stimulus-input pattern comprises a clinically validated stimulus-response pattern for treating or targeting one or more neurological, psychological and/or somatic condition in the user;

receiving a plurality of user activity data for a session of the software build, wherein the plurality of user activity data comprises a plurality of user inputs in response to the one or more computerized stimuli or interactions within the instance of the software build;

communicating, via a network communications protocol comprising an application programming interface, the plurality of user activity data from a first server communicably engaged with the user computing device to a second server, wherein the first server comprises a software development subsystem server and the second server comprises a design control sub system server;

receiving, at a classification module executing on the second server, the plurality of user activity data, wherein the classification module is communicably engaged with a design control subsystem database via a simple notification service or a simple queue service, wherein the design control subsystem database is configured to store the plurality of user activity data;

processing, via the classification module executing on the second server, the plurality of user activity data to determine one or more actual stimulus-input patterns for each user input in the plurality of user inputs, wherein the classification module comprises a computer-implemented machine learning framework comprising an ensemble learning model or a supervised learning model configured to classify one or more variables between the user activity data and the clinically validated stimulus-response pattern, wherein the classification module is configured to calculate a degree of conformity between the one or more actual stimulus-input patterns and the clinically validated stimulus-response pattern for treating or targeting the one or more neurological, psychological and/or somatic condition in the user;

comparing the one or more actual stimulus-input patterns for each user input in the plurality of user inputs to the expected stimulus-input pattern for the at least one feature to determine a total number of instances in which the one or more actual stimulus-input patterns was reflective of the expected stimulus-input pattern within the session of the software build;

calculating at least one output value for the plurality of user activity data according to the classification module, wherein the at least one output value comprises a qualitative or quantitative degree of conformity between the one or more actual stimulus-input patterns and the expected stimulus-input pattern for the at least one feature;

calculating a measure of net therapeutic activity within the session of the software build according to the total number of instances in which the one or more actual stimulus-input patterns was reflective of the expected stimulus-input pattern within the session of the software build; and determining a pass/fail status for the software build according to the at least one output value and the measure of net therapeutic activity within the session of the software build, wherein determining the pass/fail status comprises determining a minimum performance threshold for the session of the software build, wherein the minimum performance threshold comprises a minimum degree of conformity between the one or more actual stimulus-input patterns and the clinically validated stimulus-response pattern for treating or targeting the one or more neurological, psychological and/or somatic condition in the user, and wherein the minimum performance threshold comprises a minimum measure of therapeutic activity delivered to the user within the session of the software build.

* * * * *